(12) United States Patent
Deck et al.

(10) Patent No.: US 8,231,547 B2
(45) Date of Patent: Jul. 31, 2012

(54) PUNCTURING SYSTEM FOR WITHDRAWING A BODY FLUID

(75) Inventors: Frank Deck, Niederkirchen (DE);
Ortrud Quarder, Heidelberg (DE);
Thomas Weiss, Mannheim (DE);
Christian Hörauf, Oftersheim (DE);
Michael Keil, Ludwigshafen (DE);
Ahmet Konya, Mannheim (DE);
Herbert Harttig, Neustadt (DE); Felix Baader, Schweiz (DE); Hans List, Hesseneck-Kailbach (DE); Karl-Peter Ebert, Fränkisch-Crumbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1353 days.

(21) Appl. No.: 11/849,280

(22) Filed: Sep. 1, 2007

(65) Prior Publication Data

US 2008/0082023 A1    Apr. 3, 2008

Related U.S. Application Data

(63) Continuation of application No. PCT/EP2006/001922, filed on Mar. 2, 2006.

(30) Foreign Application Priority Data

Mar. 3, 2005 (DE) .......................... 10 2005 009 652
Dec. 15, 2005 (EP) ...................................... 05027429

(51) Int. Cl.
*A61B 5/00* (2006.01)
(52) U.S. Cl. ..................................................... 600/583
(58) Field of Classification Search .................. 600/583, 600/584; 606/181–183
See application file for complete search history.

(56) References Cited

U.S. PATENT DOCUMENTS

| | | | |
|---|---|---|---|
| 3,789,830 A | 2/1974 | Malmstrom | |
| 4,442,836 A | 4/1984 | Meinecke et al. | |
| 4,469,110 A | 9/1984 | Glama | |
| 4,895,147 A * | 1/1990 | Bodicky et al. | 606/182 |
| 5,029,583 A | 7/1991 | Meserol et al. | |
| 5,318,584 A | 6/1994 | Lange et al. | |
| 5,514,152 A | 5/1996 | Smith | |
| 5,554,166 A | 9/1996 | Lange et al. | |

(Continued)

FOREIGN PATENT DOCUMENTS

DE   28 03 345   6/1979

(Continued)

*Primary Examiner* — Max Hindenburg
*Assistant Examiner* — Jonathan M Foreman
(74) *Attorney, Agent, or Firm* — Bose McKinney & Evans LLP

(57) ABSTRACT

The present invention provides a puncturing system for withdrawing body fluid. The puncturing system comprises a disposable puncturing unit, which includes a needle element for piercing into skin and a puncturing depth reference element with a skin contact area. The system includes a puncturing instrument which has a puncturing drive, wherein the puncturing drive is coupled by a coupling mechanism to the puncturing unit for driving the needle element to a puncturing depth, the puncturing depth being determined by the distance in the piercing direction between the skin contact area and the position of the tip of the needle at a reversal point of the puncturing movement. The puncturing depth reference element is connected to the needle element such that the puncturing depth reference element moves with the needle element during at least part of the puncturing movement. The puncturing depth reference element has a defined longitudinal position in the piercing direction relative to the needle element at least at the reversal point of the puncturing movement.

44 Claims, 17 Drawing Sheets

U.S. PATENT DOCUMENTS

| | | |
|---|---|---|
| 5,801,057 A | 9/1998 | Smart et al. |
| 5,938,679 A | 8/1999 | Freeman et al. |
| 6,306,152 B1 | 10/2001 | Verdunk et al. |
| 6,350,273 B1 | 2/2002 | Minagawa et al. |
| 6,589,260 B1 | 7/2003 | Schmelzeisen-Redeker et al. |
| 6,616,616 B2 | 9/2003 | Fritz et al. |
| 2003/0018282 A1 | 1/2003 | Effenhauser et al. |
| 2003/0083685 A1 | 5/2003 | Freeman et al. |
| 2003/0199892 A1 | 10/2003 | Kim |
| 2004/0127818 A1 | 7/2004 | Roe et al. |
| 2004/0260325 A1 | 12/2004 | Kuhr et al. |
| 2005/0085839 A1 | 4/2005 | Allen et al. |

FOREIGN PATENT DOCUMENTS

| | | |
|---|---|---|
| EP | 1 358 844 | 11/2003 |
| EP | 1 527 735 | 5/2005 |
| EP | 1 561 421 | 8/2005 |
| EP | 1 360 935 | 12/2006 |
| EP | 1 405 595 | 2/2007 |
| JP | 2003310581 | 11/2003 |
| WO | WO 97/46157 | 12/1997 |
| WO | WO 2004/091690 | 10/2004 |

* cited by examiner

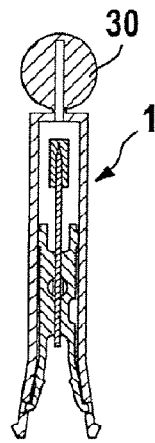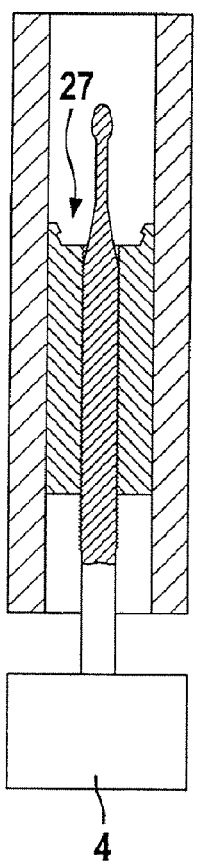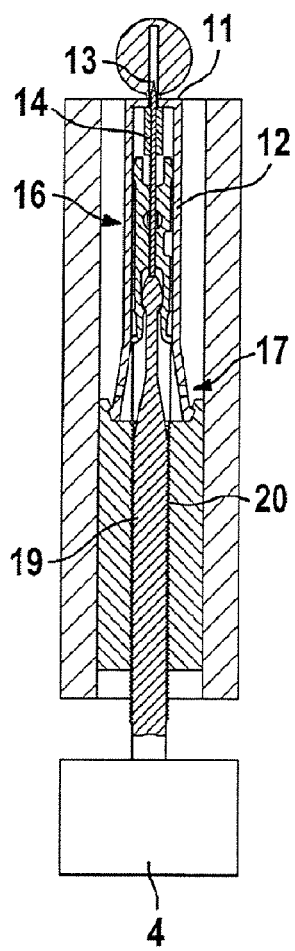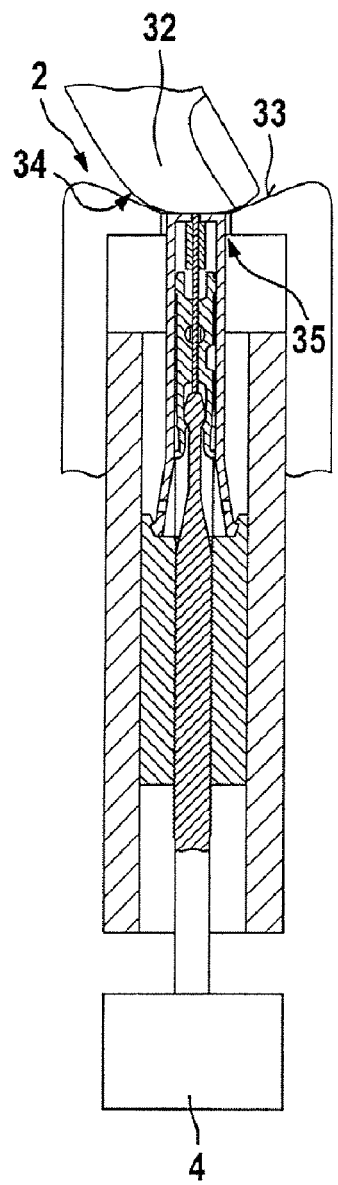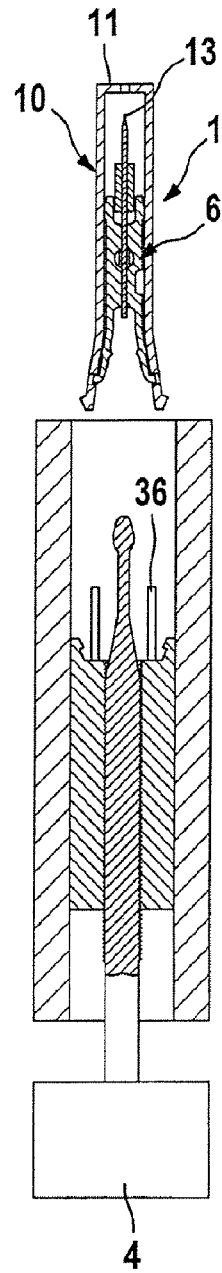
Fig. 2a    Fig. 2b    Fig. 2c    Fig. 2d

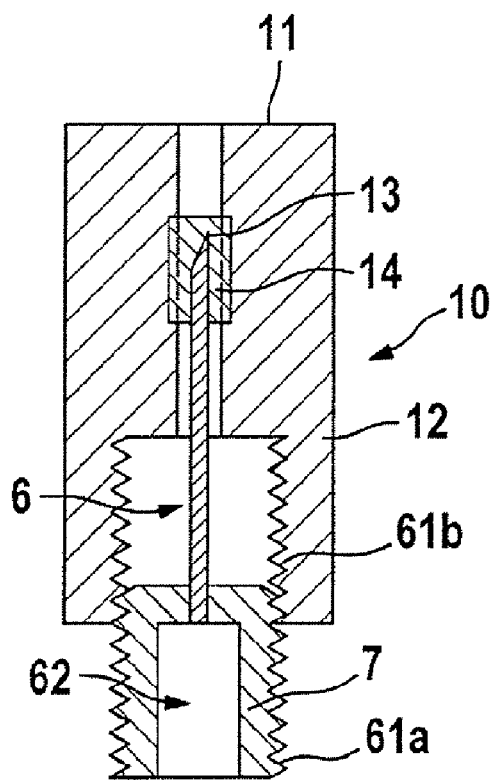
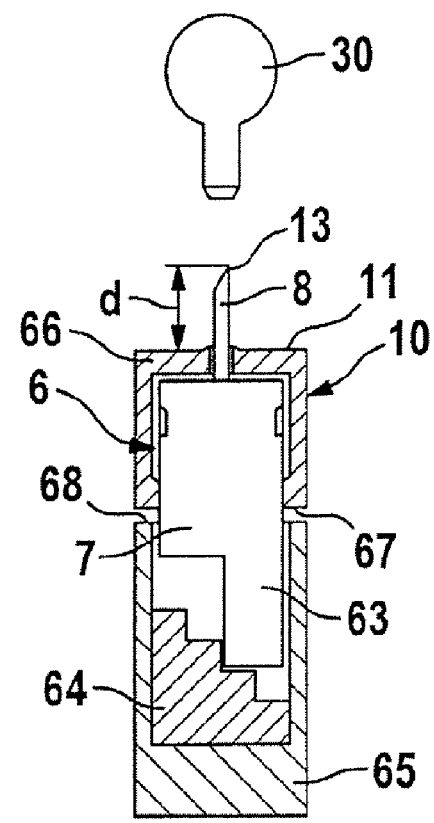
Fig. 6
Fig. 7
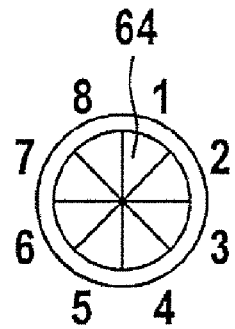
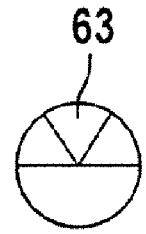
Fig. 8
Fig. 9

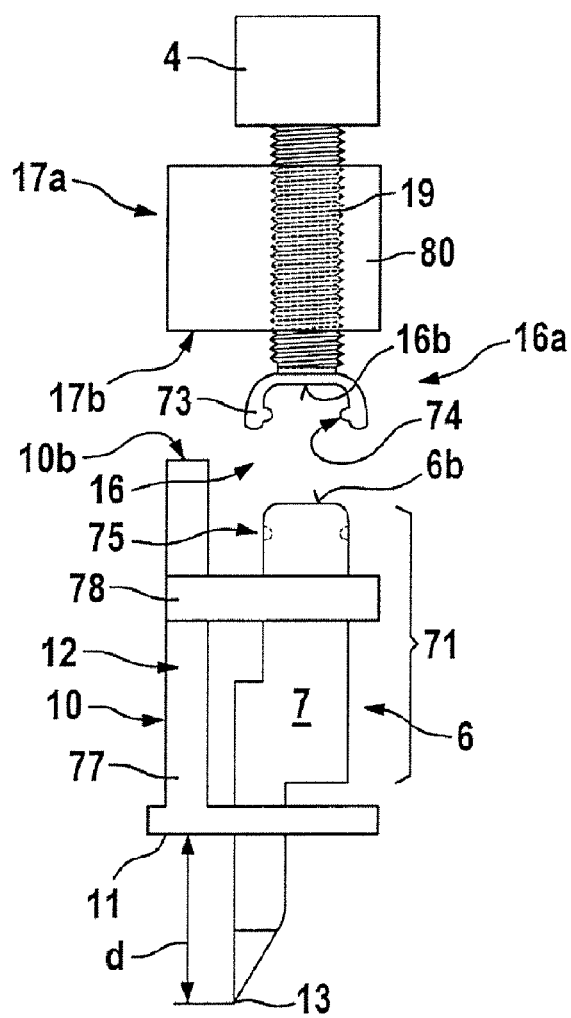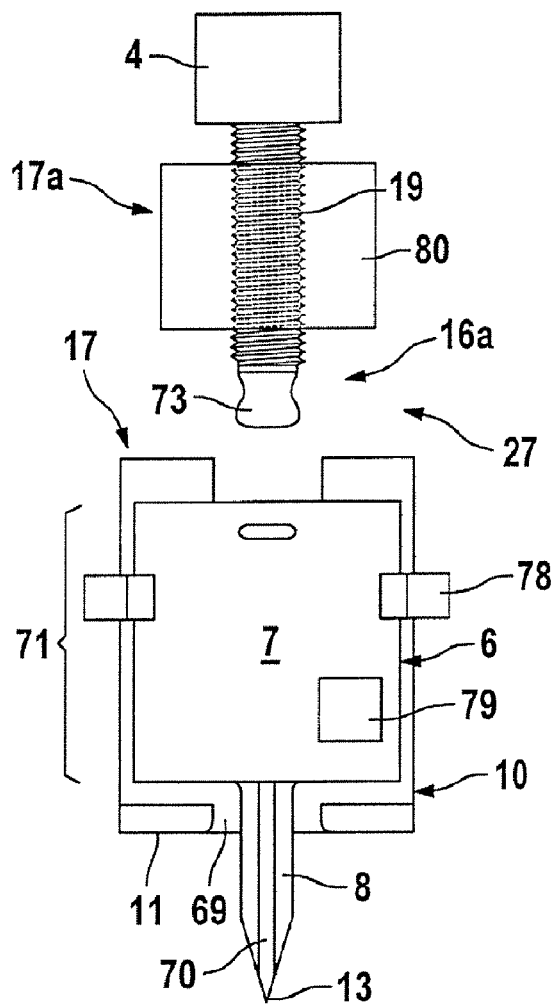
Fig. 10         Fig. 11
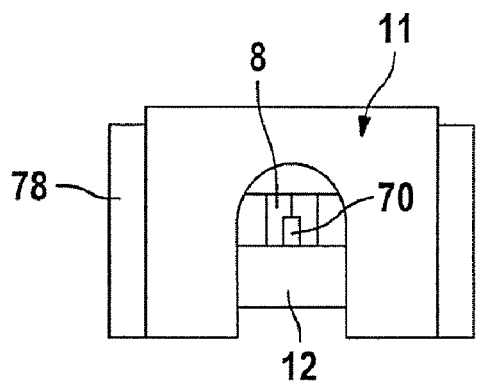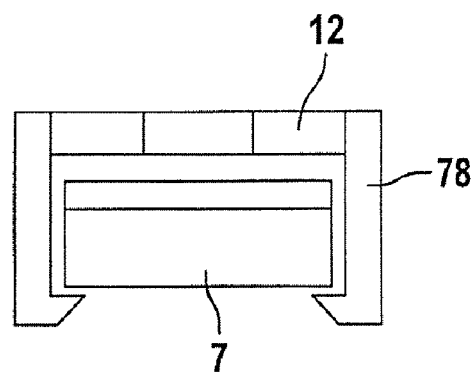
Fig. 12         Fig. 13

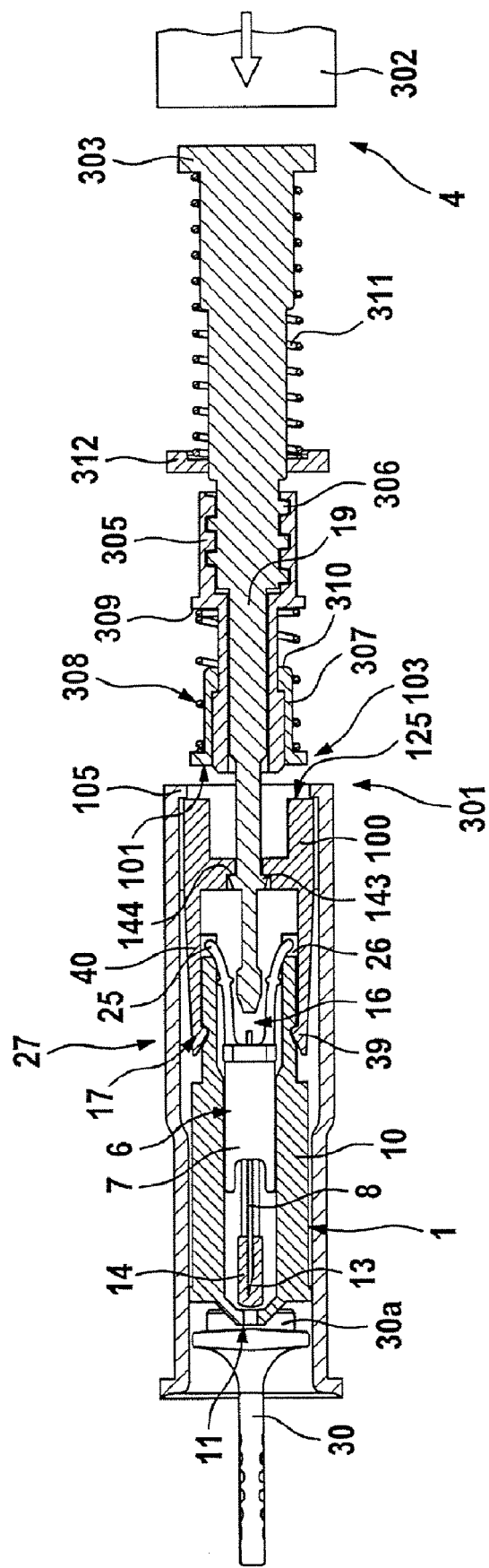
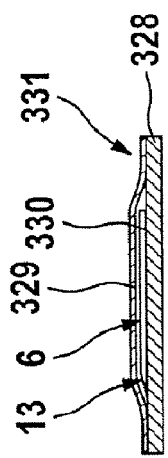
Fig. 25
Fig. 26

PUNCTURING SYSTEM FOR WITHDRAWING A BODY FLUID

RELATED APPLICATIONS

This is a continuation application of International Application PCT/EP2006/001922, filed Mar. 2, 2006, which claims priority to DE 10 2005 009 652.2, filed Mar. 3, 2005, and also claims priority to EP 05027429.9, filed Dec. 15, 2005, all of which are hereby incorporated by reference in their entirety.

BACKGROUND

Disposable puncturing units have been used to withdraw small quantities of blood from a body part (usually from a finger or earlobe) for analytical and diagnostic purposes. In this context, the puncturing units are typically designated as lancets. Lancets used for manual piercing are described, for example, in U.S. Pat. No. 3,789,830 and are typically only used by medically trained personnel. Nonetheless, the piercing can cause significant pain.

Puncturing instruments which contain a puncturing drive have been used for some time. The puncturing instrument may be a disposable item comprising a permanently integrated lancet. However, typically it is used several times and has a holder, by which a lancet may be replaceably coupled to the puncturing drive. Because the devices and lancets are elements which are mutually adapted and are provided by the same manufacturer, they are designated as a "puncturing system" or "blood withdrawal system."

Usually a spring is used as the drive element and is located in a housing of the puncturing instrument. A lancet guide makes sure that the puncturing movement occurs along a predetermined movement path. At the beginning of development, very simple constructions of the drive were typical, in which the lancet was attached directly to one end of a spring inside an elongated housing. Such a puncturing system is disclosed, for example, in U.S. Pat. No. 4,469,110. Another early design of a puncturing instrument is described in U.S. Pat. No. 4,442,836 where the lancet moves in the direction toward the skin surface (forward phase of the puncturing movement) as it is driven by a first spring, while a second spring is used to drive the retraction of the lancet (retraction phase of the puncturing movement). The second spring is effective after the force coupling between the first spring and the lancet has been interrupted.

In typical designs, the puncturing instruments have an exit opening at their front end (in the piercing direction), from which the tip of the lancet exits to produce a wound in a body part, against which the front end of the puncturing instrument is pressed. The puncturing depth is defined by the distance in the piercing direction between the position of the lancet tip in the skin at the point the lancet stops moving forward (i.e., reversal point) and the plane of the skin contact area, which annularly surrounds the exit opening and contacts the skin at the instant of piercing. The front end of the puncturing instrument typically includes the skin contact area and thus forms a puncturing depth reference element which ensures that the puncturing depth has a predefined value.

To control the puncturing depth, it is typical to limit the movement of the lancet in the piercing direction by a stop connected to the lancet which hits a corresponding stop in the housing of the puncturing instrument. This housing-stop design is disclosed, for example, in U.S. Pat. No. 4,469,110. In the case of the drive comprising two springs described in U.S. Pat. No. 4,442,836, a defined position of the reversal point of the lancet is purportedly ensured by interrupting the force transmission between the drive spring and the lancet at a defined point along the movement path.

Blood withdrawal systems of this type do not meet the requirements that are necessary to regularly monitor analytical values of blood. This is true, in particular, for diabetics needing to frequently test their blood sugar level to keep it as close as possible within specific limits by adapting insulin injections to the demand (which varies substantially as a function of food intake, physical activity, etc.). It has been proven by extensive scientific work that the most severe late-stage damage caused by diabetes mellitus (for example, retinopathy with resulting blindness of the patient) may be dramatically reduced by intensive treatment using at least four blood analyses per day.

This intensive treatment requires that the blood withdrawal process cause the least possible pain. Great progress has been achieved in this regard by the design described in U.S. Pat. No. 5,318,584, which is based, inter alia, on the finding that the pain connected with obtaining blood may be significantly reduced if the puncturing system is made in such a manner that the piercing (even if new disposable lancets are used in each case for the piercing operations) is reproducible with better quality. To achieve this, a lancet drive having a drive rotor is used. A drive spring acts on one side of the rotor (drive side) and the other side (output-side) is coupled by a coupling mechanism to the lancet in such a manner that the rotation of the drive rotor is converted into the desired puncturing movement. The output-side coupling mechanism is designed (as a control curve) in such a manner that the lancet is coupled to the drive rotor essentially without play during the entire puncturing movement (comprising a forward phase and a retraction phase) whereby the lancet movement is completely controlled by the corresponding movement of the drive rotor. The shock caused by the abutting of the two stops in a drive type including housing stops (U.S. Pat. No. 4,469,110) is avoided in this design. In addition, due to the permanent coupling without play of the lancet to the drive rotor, an exactly reproducible position of the reversal point of the lancet movement during repeated puncturing movements is ensured, which was not achieved in the drive disclosed in U.S. Pat. No. 4,442,836.

The present invention relates to a puncturing system for withdrawing a body fluid, such as blood, from the skin. The puncturing system is an integrated system that not only withdraws fluid, but also analyzes the fluid by requiring a minimum of additional handling steps by the user. This causes additional requirements, which result from the limited space if both functions are to be performed in one device which (for handling reasons) must also be as small as possible.

Integrated systems are described in U.S. Pat. Nos. 5,029,583 and 5,514,152 in which the blood is obtained by a lancet needle, whose movement in the piercing direction is limited by a housing stop, as in U.S. Pat. No. 4,469,110. In U.S. Pat. No. 5,514,152, the generated blood droplet is transferred to an analysis sensor with the aid of a capillary channel running in the device housing.

U.S. Pat. No. 5,938,679 describes a puncturing system with a puncturing unit optionally provided with capillary tubes, through which blood may be suctioned into the interior of the device with the aid of capillary forces. This is an example of a puncturing system whose needle element has a capillary channel through which a body fluid may be transported from the skin into the interior of the puncturing unit. A further example of such a puncturing system is described in U.S. Publication No. 20030018282. The puncturing unit not only comprises the needle for piercing the skin, including a capillary channel for transporting the sample, but also a detection area containing reagents. Such a puncturing unit, which simultaneously has a receiving area for the sample (formed by a capillary-active absorption layer and/or hollow chamber) and preferably also contains the reagents required for the analysis, is designated hereinafter as a "microsampler." Reference is made to the cited U.S. Publication No. 20030018282 and the documents cited therein, particularly U.S. Pat. No. 5,801,057, providing more specific details about microsamplers. Microsamplers of various designs may be used in the context of the present invention, taking into account the special features described above.

Embodiments of the present invention are generally directed to puncturing systems which include a needle element for piercing skin. The needle element can be solid or be a capillary needle (with an open capillary channel or the needle could be hollow with the capillary channel enclosed). The puncturing system produces puncturing depths suitable for use in integrated analysis systems.

SUMMARY OF THE INVENTION

An embodiment of the present invention provides a puncturing system for withdrawing body fluid and includes a disposable puncturing unit, which has a needle element for piercing into the skin, and a puncturing instrument including a puncturing drive for driving the puncturing unit. The puncturing unit is coupled by a coupling mechanism to the puncturing drive. In the forward phase of the puncturing movement, the needle element is moved along a predetermined path in a piercing direction until its tip penetrates into the skin and then in a retraction phase, the needle element is retracted after reaching a reversal point corresponding to the puncturing depth. Also, a predefined value of the puncturing depth is achieved by a puncturing depth reference element which has a skin contact area, wherein the predefined value of the puncturing depth is determined by the distance in the piercing direction between the skin contact area and the position of the needle tip at the reversal point of the puncturing movement. The puncturing depth reference element is connected to the needle element and coupled to the drive in such a manner that it is moved together with the needle element at least during part of the forward phase, and has a defined longitudinal position in the piercing direction in relation to the needle element at the reversal point of the puncturing movement.

Another embodiment includes a disposable puncturing unit for withdrawing body fluid from the skin of a human or animal comprising a needle element for piercing the skin in a piercing direction corresponding to the orientation of the needle tip and a puncturing depth reference element, by which a maximum puncturing depth of the needle is limited when a skin contact area of the puncturing depth reference element contacts the skin and a predefined value of the puncturing depth is ensured. The longitudinal position in the piercing direction of the puncturing depth reference element is adjustable in relation to the needle element. Therefore, the distance between the skin contact area and the needle tip is also adjustable to set the predefined puncturing depth.

In contrast to customary puncturing systems, in which the puncturing depth reference element is formed by a fixed component of the housing, an exemplary embodiment of the present invention provides a puncturing depth reference element which is carried along with the needle element during at least part of the forward phase. The puncturing depth is determined by the "protruding distance" of the needle tip in relation to the skin contact area, the latter being located at the front end and in the piercing direction of the puncturing depth reference element. This protruding distance is adjustable to allow the setting of various puncturing depths as a function of the requirements of the user.

The puncturing instrument may be a single-use (i.e., disposable) product in which the puncturing unit is permanently connected to the puncturing drive (via the coupling mechanism). However, in other embodiments, the puncturing instrument may be used several times and has a holder, by which a disposable puncturing unit may be replaceably coupled to the puncturing drive.

The adjustability of the needle protruding distance is achieved in one embodiment by the puncturing instrument having separate couplers for the needle element and the puncturing depth reference element. The term "coupler" is in this context to be understood as a connection by which forces are transmitted. As will be explained in more detail, for other embodiments it is sufficient if the coupler only acts in one direction (unidirectionally). However, it is advantageous for at least the needle element coupler to act bidirectionally. In any case, the coupler includes a positioning part having a stop which cooperates with a corresponding stop of the needle element or the puncturing depth reference element in such a manner that the longitudinal position of the needle element or the puncturing depth reference element is, at least at the reversal point of the puncturing movement, determined by the contact of the stops. The needle protruding distance is determined by the relative position in the puncturing direction of the two positioning parts and is thus adjustable by changing this relative position.

According to one embodiment, the needle protruding distance is set before the start of the puncturing movement and then remains constant at least up to the reversal point, i.e., during the forward phase of the puncturing movement. Therefore, the puncturing depth reference element is moved during the forward phase at the same speed as the needle element (i.e., the puncturing depth reference element moves with the needle element). According to another embodiment, the relative longitudinal position of the two elements of the puncturing unit changes during the forward phase. However, in any case, the relative longitudinal position must have a defined value at the instant at which the puncturing movement reaches the reversal point. This value corresponds to the predetermined value of the puncturing depth.

While in exemplary embodiments, the puncturing depth element includes a skin contact area which is moved during the puncturing movement, a fixed skin contact area may be provided. In one embodiment, a fixed skin contact area is provided at the front end of the puncturing instrument, which annularly surrounds a housing opening and by which the instrument is pressed against the skin during use. In contrast to known devices, however, this fixed skin contact area is not used as a puncturing depth reference. Instead, the puncturing depth reference is formed by the puncturing depth reference element skin contact area.

The housing opening enclosed by the housing skin contact area has a relatively large diameter of, for example, at least 3 mm, and advantageously at least 5 mm. Such a relatively large opening allows additional functions which are advantageous in integrated systems for the blood sampling analysis. When the device is pressed onto the skin, the skin bulges because of its elasticity into the relatively large opening. The extent to which this bulging of the skin into the housing opening occurs is a function of various factors, in particular, the contact pressure and the elasticity of the skin. This causes a variance in the position of the skin surface, which is designated hereinafter as the "Z variance." Embodiments of the present invention allow good reproducibility of the puncturing depth in spite of this Z variance.

According to one embodiment, the puncturing instrument is equipped with a "stroke adaptor," by which the reversal point of the puncturing movement is at least partially adapted to the actual position of the skin surface and thus the Z variance occurring during use of the puncturing system is partially compensated. Accordingly, the term "stroke adaptor" is used to designate a device for adapting the puncturing movement, by which an approximate adaptation of the longitudinal position of its reversal point to the actual position of the skin surface is achieved. The stroke adaptor may therefore also be designated as a stroke adaptation mechanism. Various exemplary embodiments are possible and may include the following:

(1) A design in which the actual position of the skin surface is detected (e.g., using mechanical, electronic, or optical-electronic means) and the puncturing movement is adapted to the actual position of the skin surface (before or during the forward phase) by a control means, which acts on the puncturing drive, such as its positioning in the puncturing instrument, or the coupling mechanism, and is designated as an "actively controlled stroke adaptor."

(2) Alternatively, the stroke adaptor may be implemented by an elastic element which causes "buffering" of the puncturing movement. This elastic element may be a component of the puncturing drive or of the coupling mechanism between the puncturing drive and lancet. The buffering may also be achieved by elastic mounting of the puncturing drive. A particularly suitable elastic element is a metal spring, but elastic elements which comprise elastomeric materials including rubber may also be used.

(3) The stroke adaptor may also be implemented using a friction coupling, in which two coupler elements are connected to one another by means of friction in a manner that they allow the transmission of a limited force in the direction of the puncturing movement, but, if a force acting on the coupler exceeds a limiting value, the two elements are movable relative to each other in such a manner that the force transmission in the direction of the puncturing movement is interrupted.

These design principles may also be used in combination.

Embodiments of the present invention advantageously achieve reproducible puncturing depths by providing a space-saving design which is mechanically relatively simple. It is thus especially suitable for integrated systems, in which the most compact design possible is desired for the reasons explained above. Due to the relatively simple construction, the device can be produced at favorable cost.

A further advantage results because the reproducibility of the puncturing depth is largely independent of the construction of the puncturing drive. An exemplary embodiment may be implemented in combination with different puncturing drive variants. In particular, the drive speed and further details of the puncturing movement may be adapted to the particular requirements. If necessary, the drive may be such that the puncturing unit is rapidly retracted after the piercing and thus provides space for subsequent analysis functions, in particular, the transporting of the sample into an analysis element.

In several embodiments, a type of puncturing drive is advantageous in which a solid (non-elastic) drive element is moved from a starting position into a final position and this movement of the drive element is transformed by the coupling mechanism into the puncturing movement. The drive element may be a rotor rotating around a central axis, but other drive elements, such as pivot or knee levers, are known and are suitable for the present invention depending on the requirements in the specific case. The movement of the drive element is driven by spring force or other known means, for example, electrically or electromagnetically.

In any case, the puncturing drive generates a translational movement of the needle element between a starting position and the reversal point of the puncturing movement. The distance between these points of the movement of the puncturing unit is designated as the stroke of the puncturing movement.

The present invention is explained in more detail hereinafter on the basis of advantageous embodiments shown in the figures. The special features shown therein may be used individually or in combination to provide embodiments of the present invention.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein:

FIGS. 2*a*-2*d* are cross-sectional views illustrating four operational steps of the puncturing system of FIG. 1;

FIG. 6 is a schematic cross-sectional view of a puncturing unit;

FIG. 7 is a schematic cross-sectional view of a different embodiment of a puncturing unit;

FIG. 8 is a schematic view of a lancet receptacle of the puncturing unit of FIG. 7;

FIG. 9 is a schematic view of the bottom of a lancet of the puncturing unit of FIG. 7;

FIG. 10 is a side view of a further embodiment of a puncturing unit embodied as a microsampler and a coupling mechanism of an associated puncturing instrument which forms a puncturing system with the microsampler;

FIG. 11 is a front view of the puncturing system of FIG. 10;

FIG. 12 is a bottom view of the microsampler of FIG. 10;

FIG. 13 is a top view of the microsampler of FIG. 10;

FIG. 25 is a side view, partially shown as a cross-sectional view, of a farther embodiment of a puncturing system;

FIG. 26 is a schematic cross-sectional view of a needle element strip;

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Hereinafter, "front" and "rear" are used to identify the positions of components relating to the piercing direction. Thus, for example, the end of the puncturing unit or puncturing instrument where the piercing occurs is designated as the front end and the opposite end is designated as the rear end. The terms "longitudinal direction" and "longitudinal position" relate to the spatial direction of the puncturing movement, which is also designated as the Z direction and corresponds to the main axis of typical elongated ("pencil-shaped") puncturing instruments.

Figure 1:
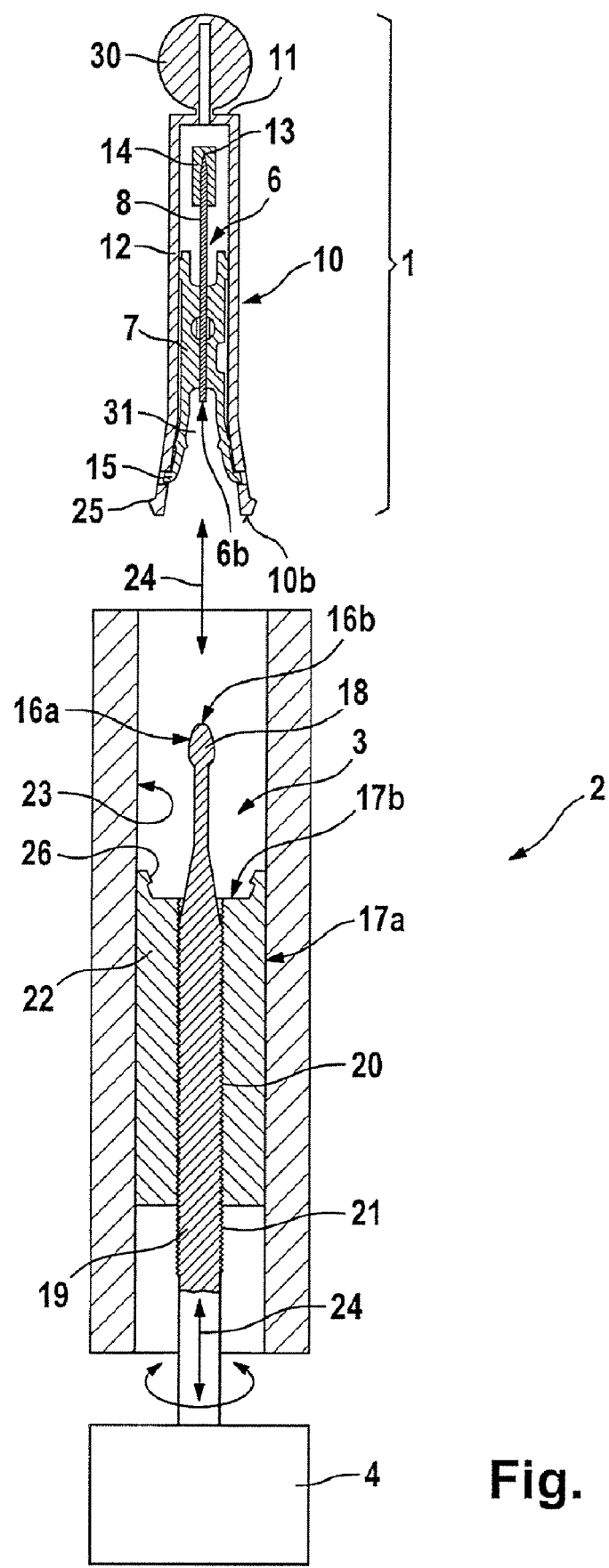
FIG. 1 is a schematic cross-sectional view of a first embodiment of a puncturing system.

FIGS. 1 and 2 show components which are important for the function of a puncturing system, such as a disposable puncturing unit 1 and parts of a puncturing instrument 2 (not shown in its entirety). These parts mainly form the coupling mechanism 3 for connecting a puncturing unit 1 to a puncturing drive 4 (only symbolically shown in these figures).

The puncturing unit 1 has two main components, namely a needle element 6 which includes a needle element body 7 and a needle 8, and a puncturing depth reference element 10 having a skin contact area 11 and a reference element body 12, which extends from the skin contact area 11 to the rear and encloses the body 7 of the needle element 6. When the needle 8 is located in the operational position, as shown in FIGS. 1 and 2a, its tip 13 is enclosed by a sterile protector 14, preferably made from a plastic material which tightly encloses the needle tip 13 and thus ensures its sterility during the storage of the puncturing unit 1.

FIGS. 1 and 2a show the delivery (before use) state of the puncturing unit 1. In this state, the needle element 6 is fixed by a fixing means 15 in a defined longitudinal position inside the reference element body 12. The fixing means 15 (for example, in the form of nubs shown engaging in matching recesses) are implemented in such a manner that the fixing is disengaged during the usage of the puncturing unit (or at least during the puncturing movement) when a relative displacement of the needle element 6 in relation to the puncturing depth reference element 10 is necessary, as will be explained below.

The coupling mechanism 3 has separate couplers for the elements of the puncturing unit 1, namely a needle element coupler 16 and a reference element coupler 17. Each of the couplers includes a positioning part 16a or 17a comprising a stop 16b or 17b, which cooperates with a corresponding stop 6b of the needle element 6 or 10b of the puncturing depth element 10 in such a manner that, in the coupled state of the elements, their longitudinal position is determined, at least at the reversal point of the puncturing movement, by the contact of these stops.

In the illustrated embodiment, the positioning part 16a of the needle element coupler 16 is formed by the thickened head 18 of a connecting rod 19, via which the needle element positioning part 16a is connected to the puncturing drive 4. The front face of the head 18 forms the stop 16b. The corresponding stop 6b of the needle element 6 is formed by the rear end of the needle 8. Such a construction of the needle element coupler is known from U.S. Publication No. 20040260325, which is hereby incorporated by reference.

A sliding body 22, which is seated in a cylindrical bore 23, is used as positioning part 17a of the reference element coupler 17. It has an axial bore with an internal thread 20, into which the connecting rod 19, which has a corresponding external thread 21, is screwed. By mutual rotation of the positioning parts 16a, 17a formed by these components, their longitudinal position in relation to one another can be changed. Advantageously, the reference element positioning part 17a (formed here by the sliding body 22) is rotationally fixed and axially displaceable, while the needle element positioning part 16a (formed here by the head 18 of the positioning rod 19) is connected to a component (here the connecting rod 19) whose position is changeable in the longitudinal direction by rotation around its own axis within the reference element positioning part 17a.

During the puncturing movement, which comprises a forward phase and a retraction phase shown in FIG. 1 by a double arrow 24, the sliding body 22 and the bore 23 act as a guide, whereby the puncturing movement takes place precisely in accordance with the predefined piercing direction.

The reference element coupler 17 in the embodiment shown is designed as a catch hook construction. Catch hooks 25 are provided at the rear end of the reference element body 12, which yields elastically in the radial direction, and engage, upon insertion of the puncturing unit 1, in a corresponding catch profile 26 provided at the front face of the sliding body 22. Stops 17b and 10b are formed by a front face of the sliding body 22 and the rearmost end of the reference element body 12, respectively.

The needle element coupler 16 and the reference element coupler 17 together form a holder 27, by which one disposable puncturing unit 1 may be coupled interchangeably to the puncturing drive 4 of a puncturing instrument 2, and which is capable of being used several times. The insertion of the puncturing unit 1 into the holder 27 is shown partially in FIGS. 2a-2b.

For easier handling, the puncturing unit 1 has an insertion aid 30 molded, for example, by plastic injection molding. It is twisted off by the user after the insertion. During insertion, the puncturing unit 1 is moved from the starting position, shown in FIG. 2a, into the position shown in FIG. 2b, in which both the needle element coupler 16 and the reference element coupler 17 are closed. A fixed connection acting in both axial directions (bidirectional) is formed between the connecting rod 19 and the needle element body 7 and between the sliding body 22 and the reference element body 12. A receptacle 31 provided at the rear end of the needle element body 7 encloses the head 18 of the connecting rod 19. The catch hook 25 engages with the corresponding catch profile 26. According to FIGS. 2a-2b, the sterile protector 14 has been shifted from the needle tip 13 to the rear of the needle due to the relative movement between the needle element 6 and the puncturing depth reference element 10.

Setting the distance in the longitudinal direction between the stops 16b and 17b may take place before the insertion of the puncturing unit 1, wherein the needle element 6 is displaced forward during the insertion procedure (while disengaging the fixing means 15) until the needle tip 13 exits from the skin contact area 11 such that the protruding distance corresponds to the desired puncturing depth. However, embodiments are also provided in which the setting of the puncturing depth takes place after the insertion of the puncturing unit. In any case, the exact desired puncturing depth may be set by changing the relative longitudinal position of the positioning parts 16a, 17a. If the setting takes place before the puncturing movement, the protruding distance of the needle tip 13 in relation to the skin contact area 11 remains constant during the puncturing movement and the position of the puncturing unit 1 is determined during the entire puncturing movement by the actual position of the connecting rod 19.

FIG. 2c shows the system components at the moment of piercing into a finger tip 32. The skin rests on a housing skin contact area 33, which is inclined inward (toward the main axis of the device) and conically towards the rear end, and which surrounds the piercing site. It is implemented at the front end of the puncturing instrument 2. The housing skin contact area 33 provides a sufficiently defined longitudinal position of the skin surface 34 surrounding the puncture site relative to the puncturing drive 4. The puncturing depth is determined by the distance of the needle tip 13 from the skin contact area 11. Because the housing opening 35 is relatively large, the skin surface 34 bulges into the housing opening 35. The extent of this bulging is a function of various factors, in particular, the contact pressure and the elasticity of the skin. It results in the above-mentioned Z variance of the puncture site of the skin surface 34.

FIG. 2d shows the system components at the time the puncturing unit is ejected. For this purpose, an ejector is provided, for example, in the form of the rod 36 shown here, which is moved forward by means of a drive (not shown) to eject the puncturing unit 1. The design is such that the puncturing depth reference element 10 is first shifted forward, while the needle element 6 remains fixed. Due to the resulting relative displacement between elements 6 and 10, the needle tip 13 retracts back behind the skin contact area 11 until it is located in a protected position in the interior of the puncturing depth reference element 10. Therefore, the danger of causing injury by the sharp needle tip 13 and the risk of infection connected thereto are reduced.

Figure 3:
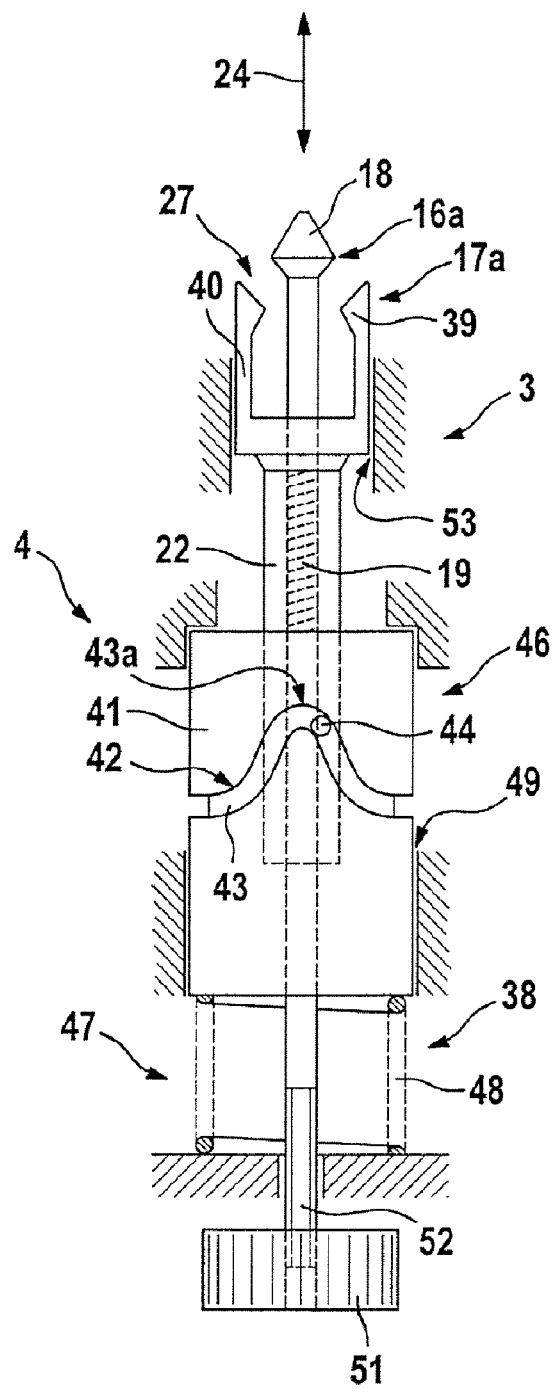
FIG. 3 is a schematic side view of a first embodiment of a puncturing drive comprising a stroke adaptor.
Figure 4:
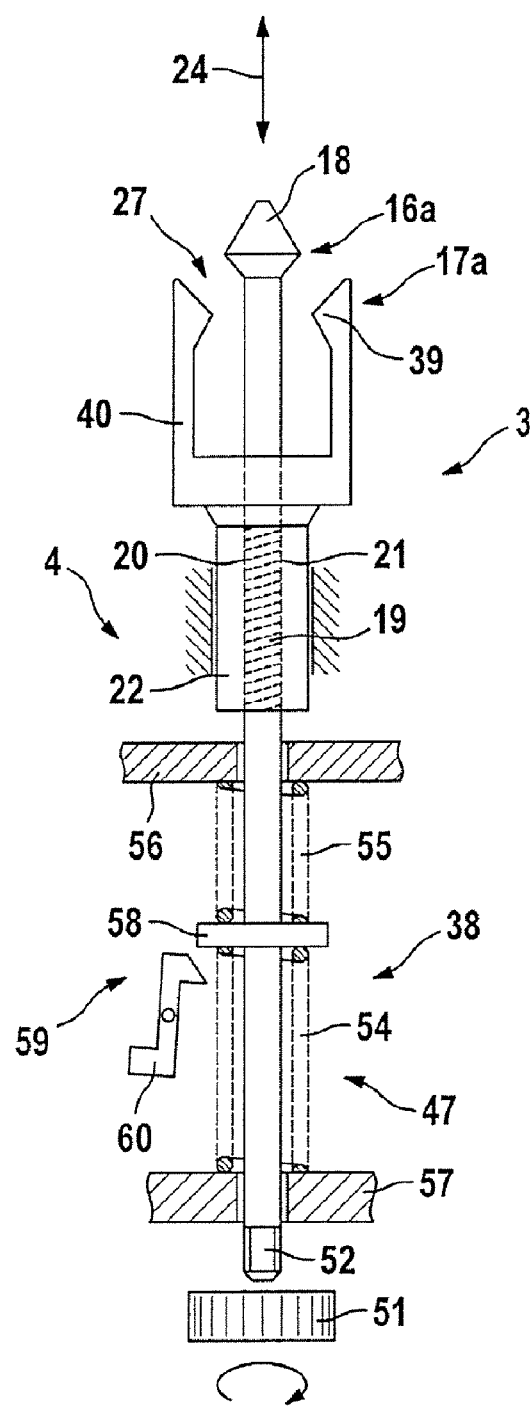
FIG. 4 is a schematic side view of a second embodiment of a puncturing drive.

FIGS. 3 and 4 show two embodiments of a puncturing drive 4, which have a stroke adaptor designated in general by 38, to adapt the puncturing movement to the actual position of the skin surface (within the Z variance possible between different puncturing actions). Similar to the embodiments of FIGS. 1 and 2, the coupling mechanism 3 has a connecting rod 19 with an external thread 21. It is seated in a corresponding threaded hole 20 of a sliding body 22. Again the head 18 of the threaded rod 19 forms a positioning part 16a of a needle element coupler, while a positioning part 17a of a reference element coupler is provided at the sliding body 22.

The mechanical design of the needle element coupler 16 and the reference element coupler 17 also corresponds to FIGS. 1 and 2. The positioning parts 16a, 17a each have a coupler profile which cooperates with a corresponding coupler profile in a coupler area of the needle or reference element (not shown). Therefore, a (preferably bidirectionally acting) coupler having corresponding stop elements is formed.

Deviating from FIGS. 1 and 2, the positioning part 17a shown in FIGS. 3 and 4 is formed by inwardly directed (toward the axis of the connecting rod 19) projections 39 of elastic arms 40. Outwardly open depressions or recesses, in which the projections 39 engage, are provided on the corresponding needle elements.

The positioning parts 16a and 17a form a holder 27 for replaceably receiving a puncturing unit. The longitudinal position of the positioning parts 16a and 17a in relation to one another can be changed by mutual rotation of the connecting rod 19 and the sliding body 22, and the needle protruding distance of a puncturing unit can thereby be set. The position of the holder 27, and thus a coupled-on or assembled puncturing unit, is determined along the puncturing movement by the actual position of the connecting rod 19.

The puncturing drive 4 shown in FIG. 3 comprises a drive rotor 41 which is used as a drive element (for example, driven by a drive spring (not shown) and after actuating a trigger (also not shown)) makes a rotational movement around its longitudinal axis, which corresponds to the axis of the connecting rod 19. The rotation of the drive rotor 41 is converted by a cam controller 42, which comprises a control curve 43 and a control curve traveler 44, into the translational puncturing movement corresponding to the double arrow 24. Rotor drives of this type are known from various publications (e.g., U.S. Pat. No. 5,318,584).

The drive rotor 41 and the cam controller 42 form a rotation-translation-transmission 46, by which the rotation of the drive rotor 41 is converted into the puncturing movement.

The reversal point of the puncturing movement is reached when the control curve traveler 44 passes through the apex point 43a of the control curve 43. The rotation-translation-transmission 46 ensures an exactly defined correlation between the actual position of the drive element (rotor) and the puncturing unit. A puncturing drive which meets this condition is designated as "positively controlled."

In the embodiment shown, a positively controlled puncturing drive is combined with a stroke adaptor using an elastic component 47. This elastic component is a coiled spring 48, which is adapted and arranged such that it forms an elastic bearing for the drive rotor 41. The rotor 41 is mounted axially displaceable in a guide hole 49 in such a manner that it may be moved rearwardly against the force of the coiled spring 48 when the skin contact area of the puncturing depth reference element contacts the skin surface during the puncturing movement. This point in time is designated as the "contact instant."

The position of the reversal point is adapted to the Z position of the skin surface by the stroke adaptor, such as by the elasticity of the elastic component 47. The elastic spring force must be arranged such that the elastic component is not significantly deformed during the puncturing movement before the contact instant. In any case, it should be undeformed immediately before the contact instant. The buffer effect should only occur upon contact of the skin contact area with the skin.

An adjustment wheel 51 is used for setting the puncturing depth. The torque transmission from the adjustment wheel, which is immobile in the axial direction, onto the axially movable connecting rod 19 may be provided by longitudinal teeth 52 of the connecting rod, which engage in corresponding internal teeth of the adjustment wheel 51.

A housing bore 53, which in the embodiment shown is positioned in the area of the elastic arms 40, is used for guiding the reference element positioning part 17a (thereby also a puncturing unit fixed in the holder 27). Space for the required elastic mobility of the arms 40 is provided by longitudinally running grooves (not shown). An axially mobile, but rotationally fixed, guide is ensured by a non-round cross-sectional design of the bore 53.

In the embodiment of the puncturing drive 4 shown in FIG. 4, a stroke adaptation is again achieved by an elastic component 47. In this case, it comprises two springs, namely a drive spring 54 and a return stroke spring 55, which are each attached on one side to a housing-fixed bearing part 56 or 57 and act on the other side via a connection flange 58 to the connecting rod 19.

FIG. 4 shows the rest state of springs 54 and 55. To cock the drive, the connecting rod 19 is moved to the rear (by means which are not shown) until a trigger element 59, which may comprise a latch 60 cooperating with the flange 58, catches. Due to the displacement of the connecting rod 19 during cocking, longitudinal teeth 52, which are again provided at the end of the connecting rod 19 in this embodiment, engage in corresponding internal teeth of an adjustment wheel 51, so that the protruding distance of the needle tip of a puncturing unit connected to the holder 27 may be set by rotating the adjustment wheel 51.

After the trigger element 59 is actuated, the connecting rod 19 is driven forward by the drive spring 54. Due to the elastic design of the drive, the forward phase of the puncturing movement ends immediately after the contact instant. The longitudinal dimensions of the components are designed such that, along the entire variance range of the position of the skin surface, the drive spring 54 is stretched beyond its rest position and the return stroke spring 55 is compressed beyond its rest position when the skin contact area of a puncturing unit hits the skin surface. As a result, the reversal point of the puncturing movement is reached immediately after the contact instant and subsequently the retraction phase is driven by the force of the return stroke spring 55.

FIG. 5 shows four functional positions (a) through (d) of a puncturing system comprising a stroke adaptor, which is implemented by a friction coupling 95. In the embodiment shown, it comprises the connecting rod 19 and pincers 96, whose arms 97 press against the connecting rod 19. In this embodiment, the connecting rod 19 connects to the holder 27 for the puncturing unit 1. Its design, including the needle element coupler, the reference element coupler, and the adjustment of the needle protruding distance by rotating the connecting rod 19, is similar to the embodiments of FIGS. 1 and 2.

Figures 5A, 5B, 5C, 5D:
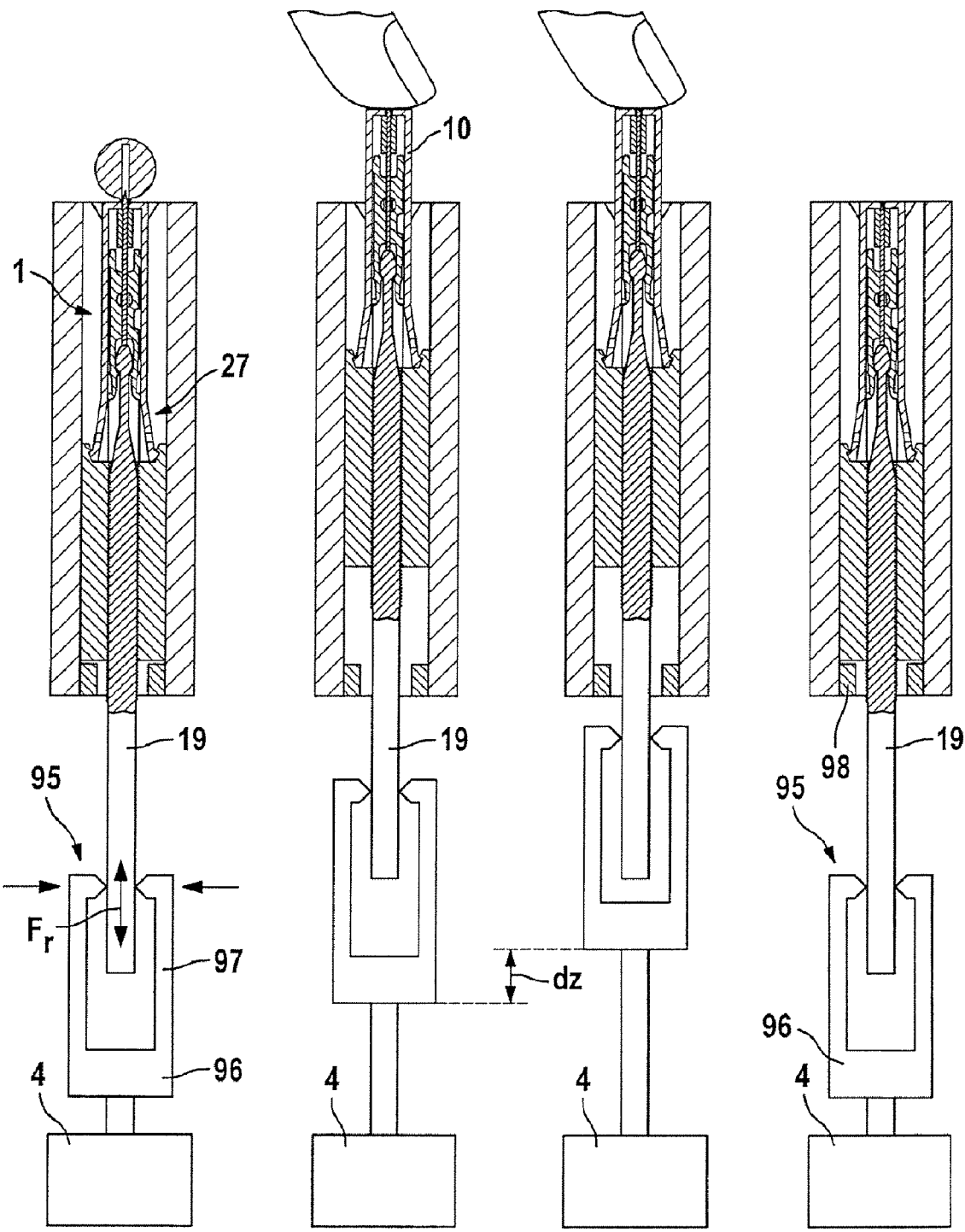
FIGS. 5*a*-5*d* are schematic cross-sectional views of four operational positions of a puncturing system comprising a second embodiment of a stroke adaptor.

The pincers 96 and the connecting rod 19 form two coupling elements of the friction coupling 95, which allow the transmission of a force in the direction of the puncturing movement. This force is designated as the friction force "Fr" and is determined by the friction between the elements of the friction coupling 95, i.e., the pincers 96 and the connecting rod 19. If the force acting between the coupling elements 19, 96 exceeds the friction force Fr, they become movable in relation to one another in such a manner that the force transmission in the direction of the puncturing movement is disengaged. This is shown in FIGS. 5a-5c. During the forward phase of the puncturing movement (i.e., between the positions shown in FIGS. 5a-5b), the friction force Fr is greater than the forces driving the forward movement in this phase, such that the relative position of the elements 19, 95 does not change.

FIG. 5b shows the contact instant. The force needed for moving the needle element forward rises significantly when the skin contact area of the puncturing depth reference element 10 contacts the skin. Thus, the force exceeds the limiting value defined by the preset friction force Fr, and therefore the elements of the friction coupling can move relative to each other, which allows the required stroke adaptation. In the embodiment shown, the stroke is reduced by an amount dz, which corresponds to the difference in position of the pincers 96 between the skin contact instant (FIG. 5b) and the maximum extension of the lancet drive 4 (FIG. 5c).

During the retraction phase of the puncturing movement, the relative position of the two coupling elements first remains unchanged until the further rearward movement of the puncturing unit holder is stopped by a suitable movement limiter 98. During the further movement of the drive 4, there is a relative movement of the elements 96, 19 of the friction coupling 95 until they are again located in the starting position.

For this function, the friction force Fr must have a defined value. It must be dimensioned in such a manner that it is greater than the sum of those forces which arise during the puncturing movement before the contact instant. These are essentially the dynamic acceleration forces for moving the accelerated masses and the static puncture forces for penetrating into the skin. On the other hand, the friction force Fr must be less than the maximum desired force with which the puncturing depth reference element 10 presses against the skin. These conditions can be fulfilled by known materials and production methods.

In the various embodiments of the stroke adaptor shown in FIGS. 3 through 5, the adaptation to the particular Z position of the skin surface is solely achieved by the elasticity of a component and/or by the friction coupling without specific control. If sufficiently comfortable piercing is not achieved, an actively controlled stroke adaptor may be used where the active control is based on the detection of the position of the skin surface, which may be performed mechanically or electronically. Of course, the electronic variant also comprises optical-electronic detection methods.

Regarding the control of the reversal point, the following basic principles can be distinguished:

a) The adaptation of the reversal point of the lancet movement may be performed before the start of the puncturing movement, particularly by shifting the puncturing drive in the longitudinal direction and thus adjusting the distance of the puncturing drive from the skin surface, such that the reversal point of the puncturing movement is closely adapted to the actual position of the skin surface. Ideally, the reversal point of the puncturing movement is forward from the position of the skin surface at the instant of skin contact. This small "stroke reserve" takes care of the elastic deformation of the skin surface upon piercing.

In this embodiment, it is favorable to use a positively-controlled lancet drive, as was described with reference to the rotor drive of FIG. 3, for example. The distance between the starting position and the reversal point of the puncturing movement, i.e., the length stroke, remains unchanged. The stroke adaptation is performed by longitudinal displacement of the stroke movement.

This embodiment provides especially precise stroke adaptation, wherein the longitudinal position of the reversal point is independent of the properties of the skin, particularly its elasticity.

b) The skin surface may be detected during the puncturing movement at or shortly before the contact instant. In this embodiment the acceleration in the direction of the skin is interrupted and the return stroke is initiated as quickly as possible after the detection.

Such an embodiment may be implemented with a relatively simple design by incorporating a sensor or sensing element at the front end of the puncturing unit. The sensor or sensing element cooperates with a control element (such as a latch), which is also mechanical, interrupts the forward phase, and initiates the retraction phase of the puncturing movement. Of course, electronic variants are also possible, in particular, comprising an electronic sensor at the front end of the puncturing unit.

In this embodiment, in contrast to the embodiment discussed above in a), the stroke of the puncturing movement is a function of the position of the skin surface. The closer the skin surface is to the puncturing drive, the sooner the forward phase is interrupted and the retraction phase is initiated, i.e., the stroke becomes shorter.

FIGS. 6 through 9 show two embodiments of puncturing units which are suitable for manual use, but may also be used as a component of a puncturing system. The longitudinal position of the puncturing depth reference element 10 in relation to the needle element 6 in the piercing direction (corresponding to the orientation of the needle) is adjustable without a puncturing instrument and means are provided by which the needle element 6 is fixed in a set position.

In the embodiment shown in FIG. 6, the body 7 of the needle element 6 and the reference element body 12 have corresponding threads, which are adapted and arranged such that their relative longitudinal position, and also the relative longitudinal position of the lancet tip 13 in relation to the skin contact area 11, is adjustable by rotation relative to each other. To bring the needle tip 13 from the rest position shown within a sterile protector 14 into an operational position, in which it protrudes from the skin contact area 1, the body 7 of the needle element 6 is rotated by a tool which engages a suitable gripping profile 62 of the body 7. This may be performed manually. Advantageously, the puncturing unit shown in FIG. 6 is used with a puncturing instrument. In this case, the setting of the puncturing depth can again be performed manually before the insertion into the puncturing instrument or it can take place within the puncturing instrument.

In the embodiment shown in FIG. 7, a support profile 63 is provided at the rear end of the body 7 of the needle element 6, which cooperates with a corresponding multistep support profile 64 of a puncturing unit receptacle 65. A possible design of the support profile in cross-section, namely as circular sectors, is shown in FIGS. 8 and 9.

In this embodiment, the puncturing depth reference element 10 is formed by a cap 66 which encloses the front section of the body 7 of the needle element. The cap 66 is fixed and frictionally-locked on the body 7. In the pre-operation status, an insertion aid 30 is seated over the needle 8. It protects the needle tip 13 and is used for the purpose of inserting the puncturing unit 1 into the puncturing unit receptacle 65 in a rotational position which corresponds to the desired puncturing depth. During insertion, the cap 66 is shifted forward in relation to the needle 8 when its lower edge 67 contacts the upper edge 68 of the puncturing unit receptacle 65. Therefore, the protruding distance d of the needle tip 13 in relation to the skin contact area 11 is set. After the insertion, the insertion aid 30 is twisted off, so that the needle 8 is exposed for use.

Numerous other embodiments of puncturing units are possible and which may also be used without a puncturing instrument. It is generally advantageous if the reference element body 12 extends from the skin contact area 11 towards the rear and encloses a body 7 of the needle element 6 at least to such an extent that the longitudinal position of the needle element 6 in relation to the puncturing depth reference element 10 is fixed by contact between the reference element body 12 and the body 7 of the needle element 6. The contact must be such that be friction-locking (as shown in FIG. 7) is achieved. Form-locking fixation of the needle element 6 within the reference element body 12 (as shown in FIG. 6) is especially advantageous for many intended uses.

FIGS. 10 to 13 show a puncturing unit which differs from the puncturing units previously shown primarily by the fact that the needle 8 of the needle element 6 has a capillary channel 70, having a lumen allowing body fluid to flow into a sample receiving area 71 of the needle element 6. Thus the needle element 6 is a microsampler of the type discussed above. Analysis elements are located in the sample receiving area 71 (in the interior of the body 7 of the needle element 6).

In this embodiment, the setting of the puncturing depth is based on adjusting the distance d of the needle tip 13 from the skin contact area 11 of a puncturing depth reference element 10 by positioning parts (16a, 17a), which are components of a needle element coupler (16) and a reference element coupler (17).

The needle element positioning part 16a is in this case implemented as a two-armed grip clamp 73. It has inwardly turned arms which are elastic and have projections 74 engaging in corresponding recesses 75 of the body 7 of the needle element 6 when the needle element coupler 16 is closed. In the closed state of the needle element coupler 16, the longitudinal position of the needle element positioning part 16a is determined by the interaction of two stops 16b, 6b, which in the embodiment shown are formed by an inner boundary face of the grip clamp 73 and by the rear face of the needle element body 7. This needle element coupler 16 acts bidirectionally, i.e., it couples the positioning part 16a to the needle element 6 in both directions of the puncturing movement.

The reference element body 12 of the puncturing depth reference element 10 essentially comprises an open frame 77, on whose bottom side the skin contact area 11 is provided, and profiled parts 78 which are transverse to the longitudinal direction and enclose the needle element 6. The skin contact area 11 surrounds an opening 69 for the needle 8 of the needle element 6.

In this embodiment, the reference element body 12 does not have to be a closed component. Rather, an open structure is also suitable if it fulfills the functions required including, for example, the needle element 6 is connected to the reference element 10 in such a manner that a relative movement of both components in the longitudinal direction is possible for adjusting the needle protruding distance d. In addition, the connection between the needle element 6 and the puncturing depth reference element 10 should provide an adequate guiding function in the longitudinal direction so that movements of both components in spatial directions other than the piercing direction are prevented.

The positioning part 17a of the reference element coupler 17 with its stop 17b is implemented at an axially guided but rotationally fixed, bearing part 80. A corresponding stop 10b is formed by the rear face of the frame 77. In this embodiment, it is a unidirectionally acting coupler, i.e., the interaction of the stops 17b, 10b, that determines the relative longitudinal position of the puncturing depth reference element 10 only during the forward phase of the piercing movement (downward in FIGS. 10 and 11).

Similar to the embodiments in FIGS. 1 through 4, the lancet drive 4 is connected via a connecting rod 19 to the puncturing unit holder 27 formed by the couplers 16, 17, the relative longitudinal position of the positioning parts 16, 17 being adjustable by rotation of the connecting rod 19 (to which the needle element positioning part 16a is attached) around its own axis within the reference element positioning part 17a (of the bearing part 80 here).

The grip clamp 73 is rotatably mounted on the end of the connecting rod 19 and is guided in the puncturing instrument in such a manner that it remains in the gripping position shown in FIG. 10 independent of the rotational position of the connecting rod 19. Electrical contacts may be provided in the area of the projections 74 of the gripping clamp 73 and the corresponding recesses 75 and electrical measurements may be performed on a sample liquid located in the sample receiving area if the puncturing unit 6 is implemented as an electrochemical microsampler. Alternatively, a window 79 may be provided in the sample receiving area 71 to allow the required photometric measurement in case of a microsampler adapted for photometric analysis. These measurement principles are known and an explanation in more detail is not necessary.

FIG. 14 shows four operational positions, (a) through (d), of a microsampler puncturing unit, whose design features correspond to FIGS. 10 through 13.

Figures 14A, 14B, 14C, 14D:
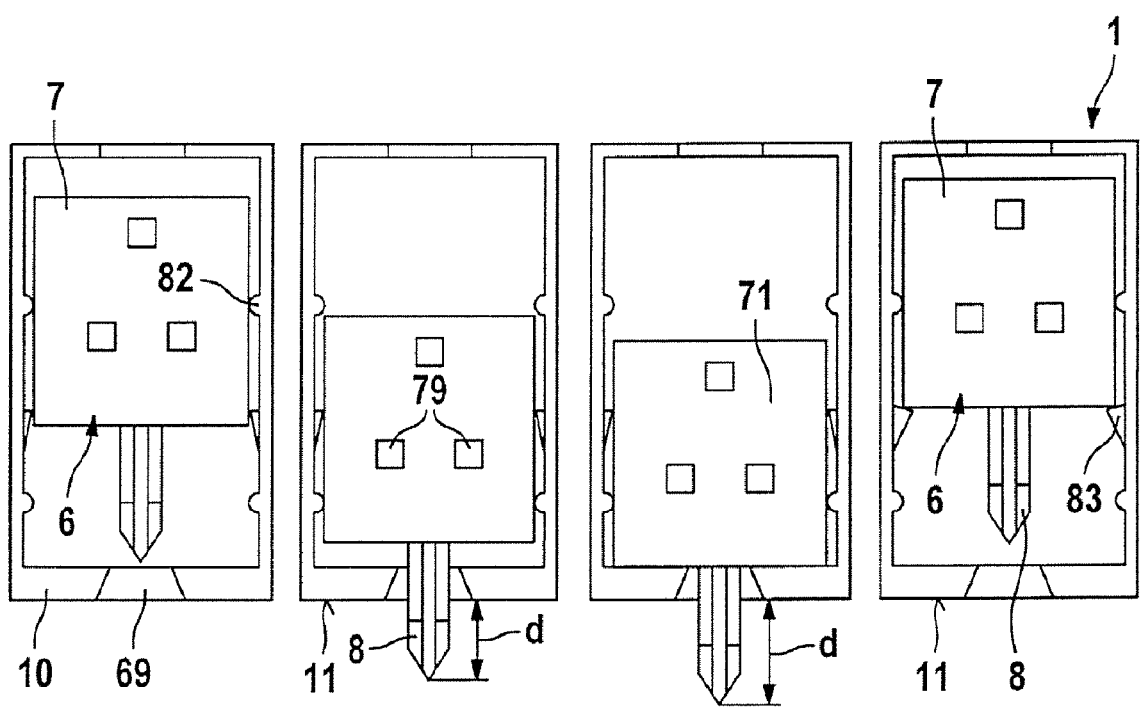
FIGS. 14*a*-14*d* are side views of a second embodiment of a microsampler illustrated in four different operational positions.

In FIG. 14a, the pre-operation state is shown, in which the needle element 6 is fixed by friction-locking in a specific longitudinal position relative to the reference element 10. This fixing is achieved by nubs 82 on the reference element 10, which press against boundary surfaces of the body 7 of the needle element 6.

FIG. 14b shows the puncturing unit at the reversal point of the puncturing movement at a relatively short needle protruding distance d, i.e., a relatively small piercing depth. During the movement from the position in FIG. 14a and FIG. 14b, the needle element coupler 16 (FIGS. 10 and 11) is first closed and the needle element 6 is pressed downward until the stops 16b, 6b abut against one another. At a later point in time during the forward phase, the contact between the stops 10b, 17b and the reference element 10 is also moved in the direction toward the skin. This movement sequence is an example showing that the puncturing depth does not have to be set before the start of the puncturing movement, but rather may also be set during its forward phase. The needle 8 penetrates into the skin and the forward phase of the puncturing movement ends when the skin contact area 11 abuts against the skin.

FIG. 14c shows the operational state at the reversal point of the puncturing movement, but at the maximum needle protruding distance d, i.e., maximum puncturing depth.

When a sufficient quantity of body fluid has flowed into the sample receiving area 71 of the needle element 6, the retraction phase of the puncturing movement is initiated and the needle element 6 is retracted into the reference element 10. The reference element 10 is fixed by means which are not shown in the figures. The needle element 6 reaches the position shown in FIG. 5d in which the needle 8 is retracted behind the skin contact area 11 to protect against a risk of injury. In this position, the body 7 of the needle element 6 is located behind blocking projections 83, which are implemented in such a manner that the needle element 6 may not be moved back into either usable position shown in FIGS. 5b-5c. By providing blocking means of this type on the reference element 12 and/or the needle element 6, the movement of the needle element 6 in relation to the reference element 10 is restricted, and after the usage of the puncturing unit 1, in such a manner that further use of a used puncturing unit 1 is prevented.

Figure 15:
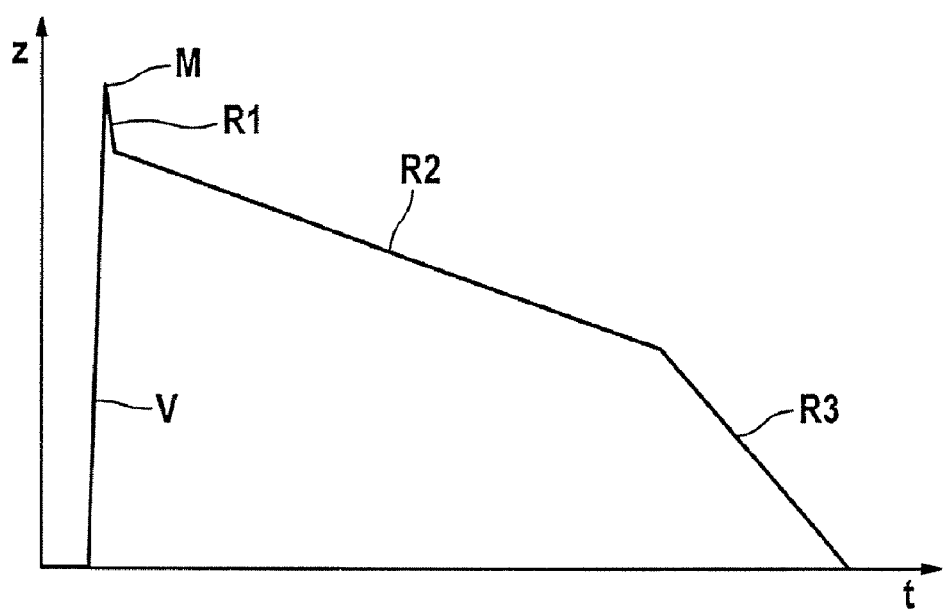
FIG. 15 is a position-time graph representative of a typical puncturing movement of a puncturing system.

The puncturing movement differs in the case of a microsampler (FIGS. 10 through 14) from the typical puncturing movement of a lancet (FIGS. 1 through 9). In the case of a lancet, the retraction phase of the puncturing movement occurs immediately after the reversal point and the puncturing movement should take place as rapidly as possible. In contrast, in the case of a microsampler, the movement of the puncturing unit during the retraction phase occurs after the reversal point is interrupted or slowed for the time needed for suctioning the body fluid. A corresponding position-time diagram or graph is shown in FIG. 15. It shows a steep rise, which corresponds to a rapid movement in the piercing direction during the forward phase V. After reaching a maximum M, which corresponds to the reversal point of the puncturing movement, a rapid retraction movement follows R1, and then a slow retraction movement R2 occurs. The portion of the retraction phase identified by R1 occurs as a small open space within the skin tissue forms in the area in front of the needle tip in which sample body fluid is collected. During the subsequent portion R2, blood or body fluid flows through the capillary channel of the microsampler into its sample receiving area. When this procedure is completed, section R3 of the retraction phase follows, in which the needle is pulled out of the skin tissue.

A movement sequence of this type which is suitable for a microsampler may be implemented in various ways. A mechanical spring drive is particularly suitable for the forward phase V and the first portion of the retraction phase R1, while the relatively slow and controlled movement during portions R2 and R3 is advantageously driven by an electric motor.

Figure 16:
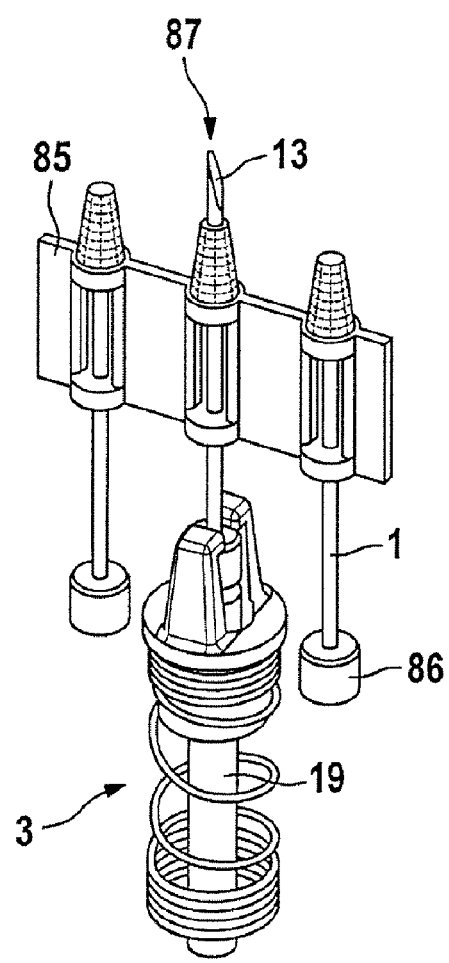
FIG. 16 is a perspective view of a puncturing system including lancets disposed in a magazine.
Figure 17:
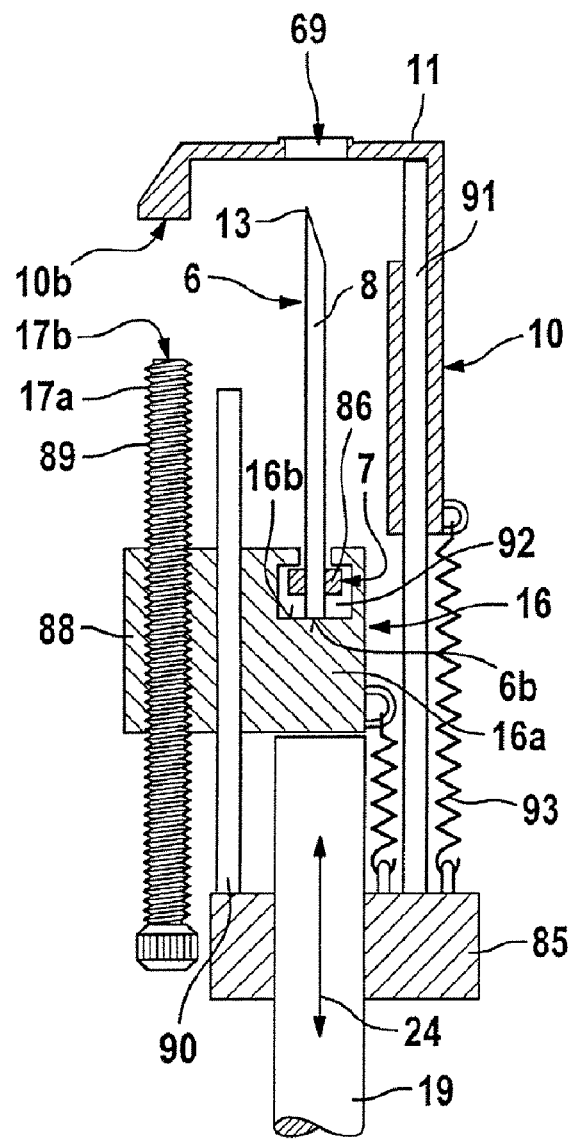
FIG. 17 is a cross-sectional view of a puncturing system including puncturing units disposed in a magazine.

FIGS. 16 and 17 illustrate that embodiments may also be used in puncturing systems in which a plurality of puncturing units are provided in a magazine and are transported in sequence into a puncture position within the puncturing instrument. A device suitable for this purpose, which is known from U.S. Pat. No. 6,616,616, is shown in FIG. 16. Lancet-shaped puncturing units 1 are located in a magazine strip 85 made of plastic, in which they are held in such a manner that they are axially movable and guided. On their rear end, they have a coupling cylinder 86 used for coupling a lancet located in a puncture position 87 to a coupling mechanism 3, which forms the connection to a puncturing drive (not shown).

FIG. 17 illustrates alternatives which may be implemented in a puncturing system including puncturing units connected in a magazine. The puncturing movement generated by a puncturing drive (not shown) is transmitted by a connecting rod 19, which makes a puncturing movement in a direction 24 relative to the magazine strip 85. In this embodiment, the coupling cylinder 86 forms the body 7 of the needle element 6. The connecting rod 19 acts on a bearing part 88, into which a set screw 89 is screwed. The bearing part 88 and the puncturing depth reference element 10, which has a skin contact area 11, are guided in the direction of the puncturing movement by guide rods 90, 91.

In this embodiment, the positioning part 16a of the needle element coupler 16 is formed by the bearing part 88. A stop 16b is formed by the bottom surface of a recess 92 provided in the bearing part 88, which receives the coupling cylinder. It cooperates with a corresponding stop 6b, which is formed in this case by the rear end of the needle 8 of the needle element 6.

In this embodiment, the reference element coupler 17 acts unidirectionally. Its positioning part 17a is formed by the set screw 89, whose front face acts as a stop 17b, which cooperates with a corresponding stop 10b of the reference element 10.

When, in the forward phase of the puncturing movement, the connecting rod 19 is moved forward (upward in FIG. 17), the needle element 6 is first moved in the piercing direction until the needle tip 13 projects out of the opening 69 surrounded by the skin contact area 11. The resulting protruding distance is determined by the longitudinal position of the set screw 89, i.e., the stop 17b implemented thereon, in relation to the stop 10b of the reference element. Upon contact of these two stops, the reference element 10 is pressed against the force of a retraction spring 93 together with the needle element 6 until the piercing occurs. The depth of the piercing is determined by the protruding distance of the needle tip 13 in relation to the skin contact area 11.

In this embodiment, the components 88, 89, and 10 are part of the magazine 85 and which are only provided once for each magazine. Alternatively, they may also be implemented as a component of the puncturing instrument. In any case, it is advantageous if, in a puncturing system including puncturing units located in a magazine, only one (i.e., shared) puncturing depth reference element 10 is provided for all puncturing units of the magazine. A transport movement occurs between the puncturing steps, whereby a new needle element 6 is brought into the operating position (shown in FIG. 17), in which it is moved during part of the puncturing movement together with the reference element to achieve the desired puncturing depth.

Other embodiments may be used in connection with different magazine designs. For example, these include drum magazines as are described in U.S. Publication No. 20040260325.

Figure 18:
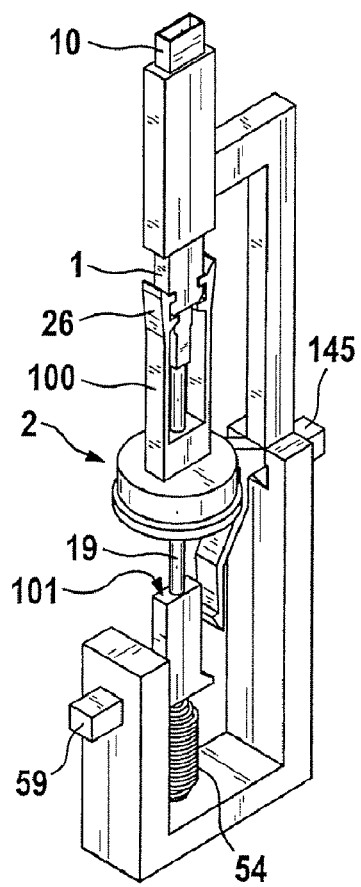
FIG. 18 is a perspective view of a further embodiment of a puncturing system illustrated without its housing.
Figure 19:
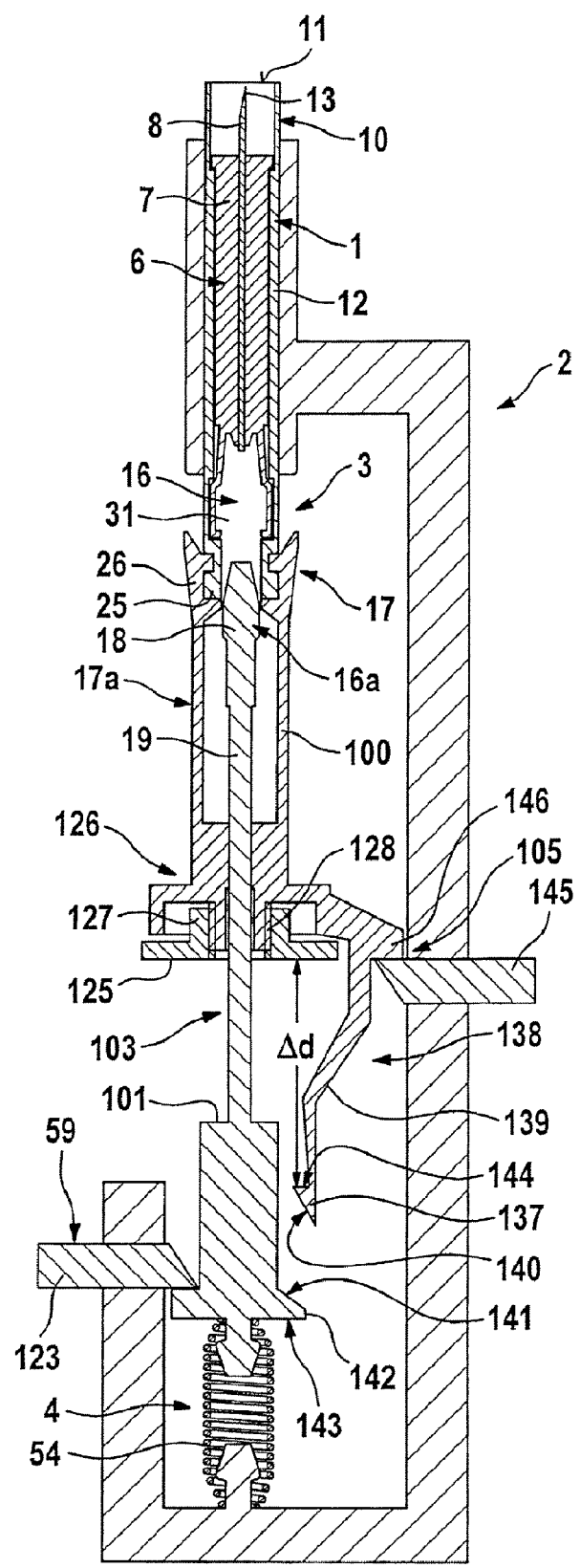
FIG. 19 is a cross-sectional view of the puncturing system of FIG. 18.

In the puncturing system shown in FIGS. 18 and 19, the design of the puncturing unit 1 and its connection to the puncturing drive 4 largely correspond to FIGS. 1 and 2. The puncturing unit 1 comprises a needle element 6 including a needle 8 and a needle element body 7 enclosing the needle and made of plastic, as well as a puncturing depth reference element 10 comprising a reference element body 12, which is sleeve-shaped in this embodiment, and a skin contact area 11.

The connection to the lancet drive 4 is provided by a coupling mechanism 3, which comprises a needle element coupler 16 and a reference element coupler 17. Corresponding to FIGS. 1 and 2, the positioning part 16a of the needle element coupler 16 is formed by the head 18 of a connecting rod 19, which engages in a corresponding receptacle 31 of the needle element body 7. The reference element coupler 17 is formed by a catch coupler comprising catch hook 25 and catch profile 26, which are implemented on puncturing depth reference element 10 and reference element holder 100, respectively. The latter is movable in the longitudinal direction of the connecting rod 19.

The puncturing system of FIGS. 18 and 19 has (corresponding to the embodiment of FIG. 4) a so-called "ballistic" puncturing drive 4, in which the puncturing movement is not "positively controlled" as defined above. In a ballistic puncturing drive, the puncturing movement is determined, near the reversal point, and advantageously along the entire movement path, by the accelerating force of one or more drive springs, the mass inertia of the components accelerated by the drive springs, and the movement of controlling or limiting stops (and also, of course, by the friction between moving components).

In the embodiment shown, a helical spring is used as the drive spring 54, which is shown in the compressed state in FIGS. 18 and 19. It is coupled to a connecting rod 19, which is accelerated by the drive spring 54 in the piercing direction after actuation of a trigger element 59. In the embodiment shown, the trigger element 59 is a bolt 123, which locks the connecting rod 19 in the retention position shown. To trigger the puncturing movement, the bolt 123 is retracted in such a manner that the connecting rod 19 can be accelerated by the drive spring 54.

The reference element coupler 17 is closed upon the insertion of the puncturing unit 1. The needle element coupler 16, in contrast, is only closed after the actuation of the trigger element during the forward movement of the connecting rod 19. Thereafter, both the movement of the needle element 6 and the movement of the puncturing depth reference element 10 follow exactly the movement of the corresponding positioning part 16a, 17a, i.e., of the connecting rod 19 and the reference element holder 100.

During the forward phase, the connecting rod 19 moves forward until its stop face 101 contacts a corresponding stop face 125 of an adjustment device 126, which is provided at the rear end of the reference element holder 100. The stop face 125 is located on the head of an adjustment screw 127, which is screwed onto a thread 128 running in the piercing direction. By rotating the adjustment screw 127, the longitudinal position of the stop face 125 in relation to the reference element 10 (and thus in relation to the skin contact area 11) may be adjusted.

In the illustrated embodiment, the puncturing drive 4 is directly coupled only to the needle element 6. The reference element 10 is coupled via a co-transport device 103 to the needle element 6 and thus indirectly to the puncturing drive 4, the co-transport device 103 acting in the forward phase of the puncturing movement. The co-transport device 103 comprises two stops 101 and 125, which abut against one another during the forward phase up to the reversal point of the puncturing movement in such a manner that their relative distance defines the longitudinal position of the needle tip 13 in relation to the contact area 11 of the puncturing depth reference element 10, and thus the puncturing depth. The stops 101, 125 are therefore designated "puncturing depth limiting stops."

At the reversal point of the puncturing movement, the drive spring 54 is stretched so that the connecting rod 19 is retracted again and thus the retraction phase of the puncturing movement starts. In the embodiment shown, the spring force of the drive spring 54 is used for accelerating the puncturing unit both during the forward phase and also during the retraction phase of the puncturing movement.

For an advantageous function of the puncturing system shown, it is also important that the reference element 10 rests, by means of a reference base part 146, on a reference element bearing 105 during a part of the forward phase and also during a part of the retraction phase. A reference base part 146 is a functional element which is connected directly or indirectly to the reference element 10 and limits, in cooperation with the reference element bearing 105, its movement path to the rear in a defined position. In the embodiment shown, it is formed by a shoulder formed on a needle element retraction limiter 138, which is connected to the reference element holder 100 and whose function will be explained in more detail.

Figure 21A:
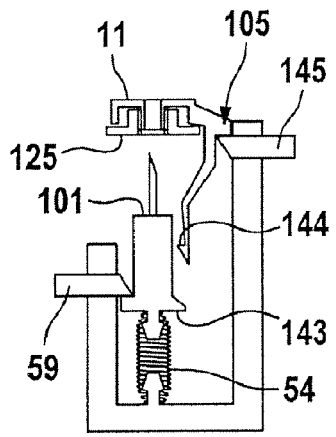
FIGS. 21*a*-21*d* are schematic side views of a puncturing system similar to FIG. 18 illustrated in four operational positions.
Figure 21B:
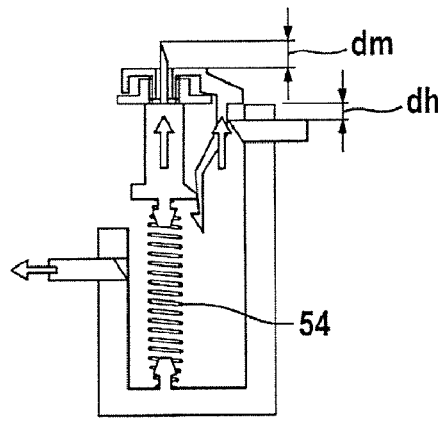
Figure 21C:
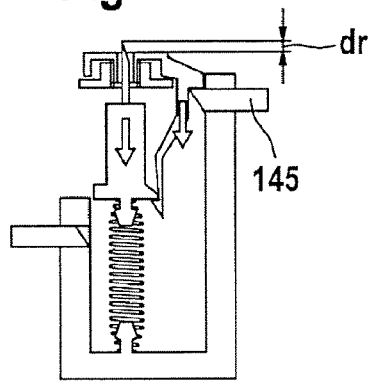

As shown in FIG. 19, the position of the reference element bearing 105 is selected in consideration with the dimensions of the remaining components in such a manner that the contact between the reference element stops 101, 125 first occurs shortly before the reversal point of the puncturing movement, so that the reference element holder 100 lifts off only by a short distance from the reference element bearing 105 until reaching the reversal point. Even if the reference element 10 can move freely in the piercing direction (i.e., does not hit a body part located in its movement path), the maximum distance dh shown in FIG. 21B, by which the reference base part 146 lifts off of the reference element bearing 105, is at most 5 mm, and generally between 2-3.5.

At the beginning of the retraction phase, the reference element 10 is moved rearwardly together with the needle element 6 by the distance dh by which the reference base part 146 was lifted off of the reference element bearing 105. This rearward movement is caused by the elasticity of a skin surface to which the skin contact area 11 abuts and, in addition, by the rearward movement of the connecting rod 19 and the needle element 6, the friction between these elements, and the puncturing depth reference element 10 or the reference element holder 100 causing sufficient force transmission.

An additional rearward movement of the reference element holder 100 and thus the reference element 10 is stopped by the reference element bearing 105, while the connecting rod 19 and needle element 6 are drawn further rearwardly by the force of the spring 54 until the movement is stopped by a stop element 137 of the mentioned needle element retraction limiter 138. In the embodiment shown, the needle element retraction limiter 138 comprises a spring element 139 in the form of a spring arm, which carries the stop element 137, implemented as a latch, on its free end. The latch has a beveled sliding face 140, which during the forward phase of the puncturing movement, slides past a corresponding sliding face 141, which is formed on a catch projection 142 provided at the connecting rod 19. During this sliding, the spring arm 139 of the needle element retraction limiter 138 yields elastically to the side. As soon as the catch projection 142 has passed the stop element 137, it returns back to its original position due to the spring force of the spring arm 139. In this position, it stops the connecting rod 19 and thus the needle element 6, wherein a stop face 143 of the catch projection 142 of the connecting rod 19 contacts a stop face 144 of the stop element 137.

The needle element retraction limiter 138 may also have a different design. In principle, any element by which the retraction movement of the puncturing unit 6 can be stopped in a defined longitudinal position is suitable. This longitudinal position is selected in relation to the longitudinal position of the skin contact area 11 provided by the reference element bearing 105 in such a manner that the tip 13 of the needle element 8 projects by a defined residual puncturing depth from the plane of the skin contact area 11.

FIGS. 18 and 19 illustrate that different coupler types may be used as a component of the coupling mechanism 3 between the puncturing drive 4 and the puncturing unit 1. The needle element coupler 18 couples the puncturing drive 4 to the needle element 6 during the forward phase of the puncturing movement and then forms a bidirectionally-acting fixed connection between these elements. The connection between the puncturing drive 4 and the reference element 6 is provided indirectly via the reference element holder 100. This holder is fixedly connected to the reference element 10, upon insertion of the puncturing unit 1 by the bidirectionally-acting reference element coupler 17. In addition, the reference element holder 100 is a component of the co-transport device 103, which includes two pairs of stops 125, 101 and 143, 144, which each form a coupler acting in one direction (unidirectional). These couplers are implemented such that the connecting rod 19 and the needle element 6 are movable relative to the reference element over a distance Δd between the stops 125 and 144. Δd corresponds to the difference between a maximum piercing depth dm and a residual piercing depth dr, as will be explained in more detail below.

Figure 20:
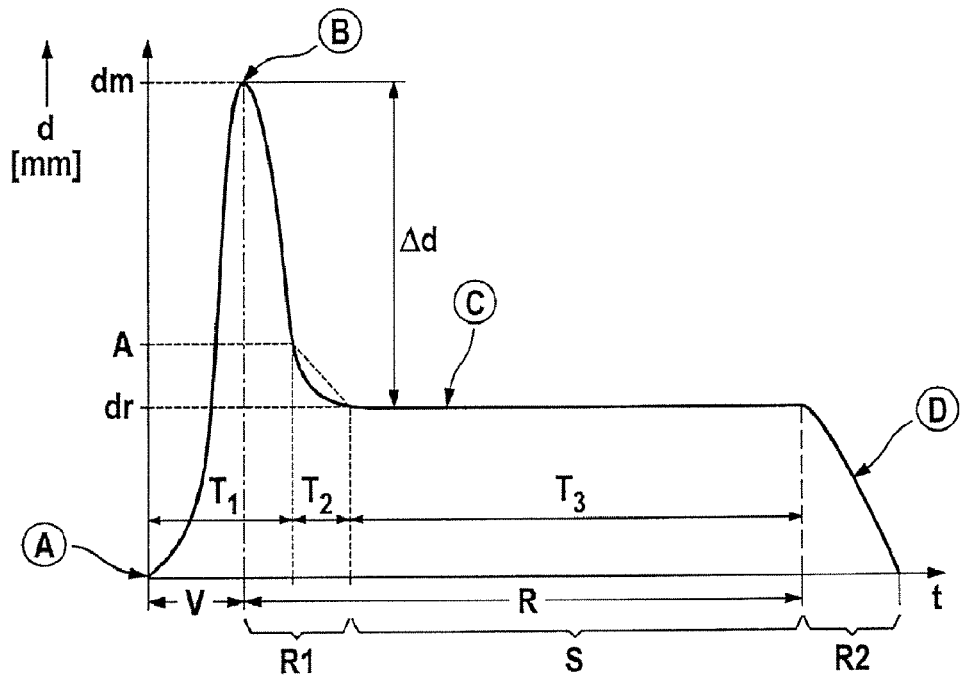
FIG. 20 is a position-time graph representative of a puncturing movement of a different puncturing system.

The puncturing movement shown in FIG. 20 in the form of a position-time diagram ("puncturing profile") may be implemented by the construction of FIGS. 18 and 19. It is suitable for microsampler puncturing systems whose needle element has a capillary channel to receive a sample. FIG. 21 shows four operational positions of a puncturing system largely corresponding to the puncturing system of FIGS. 18 and 19 wherein, some elements have been simplified with respect to details which are not significant for the functions explained herein. The corresponding moments in time relating to the operational positions (A) through (D) are marked in FIG. 20.

FIG. 20 shows the position-time curve of the piercing depth d of the needle element during a forward phase V and a retraction phase R, the retraction phase R comprising a first retraction section R1, a collection section S, and a second retraction section R2. The time axis has a varying scale. The section of the movement identified by T1 is executed within a few milliseconds, while the movement section identified by T2 (braking before the collection section) lasts several hundred milliseconds and the collecting section (T3) can last several seconds.

At the end of the forward phase V (operational position B), the puncturing element reaches a maximum piercing depth dm, which is typically between 0.8 mm to 2.3 mm depending on the setting of the puncturing instrument. This is followed by the first retraction section R1, in which the puncturing element is partially retracted by a retraction segment Δd. At the end of R1, the element still projects into the skin at a predefined residual puncturing depth dr (for example, 0.5 mm in operational position C). Finally, a second retraction section R2 follows (operational position D), in which the needle 8 of the needle element 6 is pulled completely out of the skin.

Figure 21D:
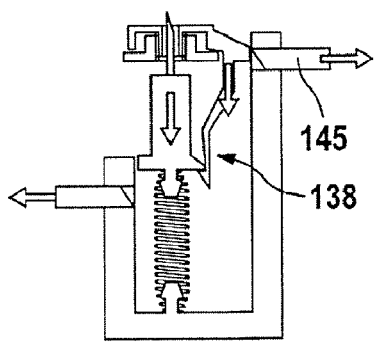

In the embodiment shown in FIGS. 19, 20, and 21, the second retraction section R2 at the end of the collection phase is initiated by removing the blocking bolt 145 from the engaged position shown in FIGS. 19 and 21A through 21C into a retracted position shown in FIG. 21D. Thereafter, the retraction limiter 138 is moved by the drive spring 54 rearwardly together with the connecting rod 19. The retraction phase is thus completed and the needle 8 of the needle element 6 is completely removed from the skin.

If the puncturing profiles shown in FIGS. 15 and 20 are compared, one difference is that the residual puncturing depth dr during the collection section S of the retraction phase practically does not change. Instead, in the embodiment shown in FIGS. 18 through 21, due to the interaction between the reference element bearing 105 and the needle element retraction limiter 138, the puncturing depth dr has a predefined and constant value. It is especially advantageous that the maximum puncturing depth dm can be set independently of the residual puncturing depth dr. In this regard, the puncturing system of FIGS. 18 through 21 differs from the previously described puncturing systems in which the setting of the puncturing depth simultaneously has an effect on the entire puncturing movement and therefore the residual puncturing depth dr, at which the sample is received in a microsampler, unavoidably changes when the maximum puncturing depth dm is adjusted.

It is advantageous to the quality of obtaining fluid samples and for the pain sensation felt during usage of microsampler puncturing systems if the residual puncturing depth dr, i.e., the puncturing depth by which the needle of the needle element projects into the skin during the collection of the sample, remains relatively constant independent of the set maximum puncturing depth. Small variations in the residual puncturing depth dr or slow movement of the needle element during the collection of the sample are acceptable. It is, however, necessary that the maximum puncturing depth dm can be adjusted independently over time relative to the residual puncturing depth dr during the collection of the sample.

Figure 22:
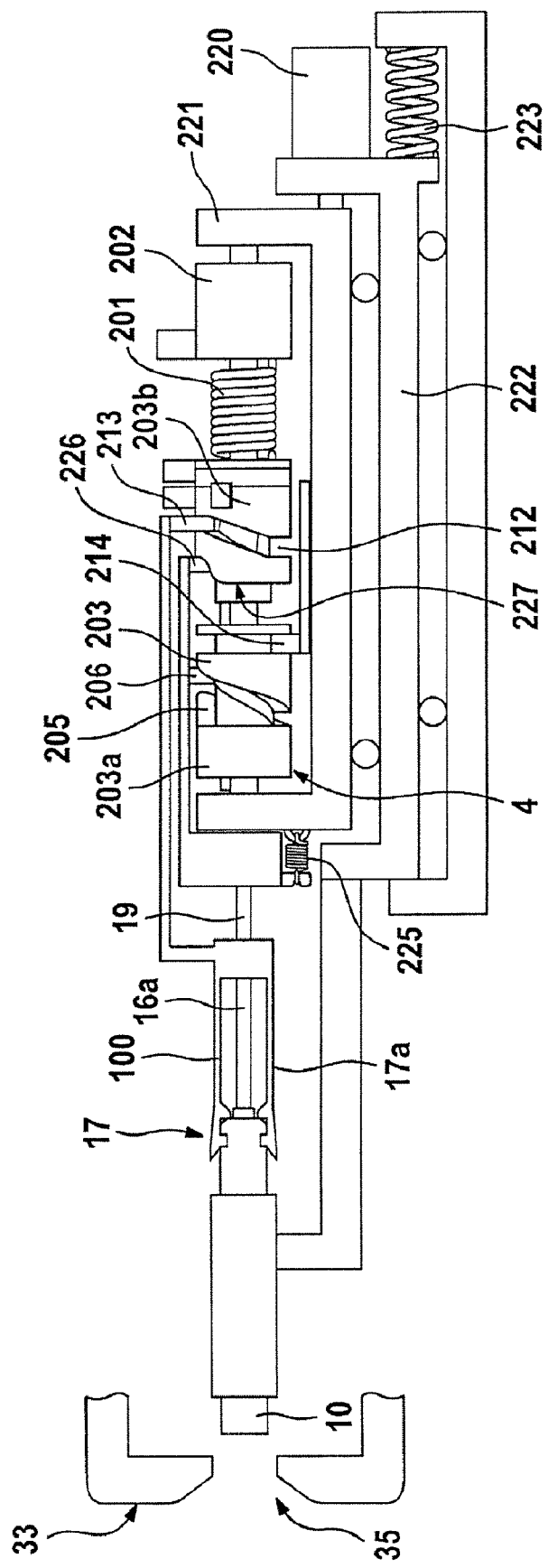
FIG. 22 is a side view of another exemplary embodiment of a puncturing system illustrated without its housing.
Figure 23:
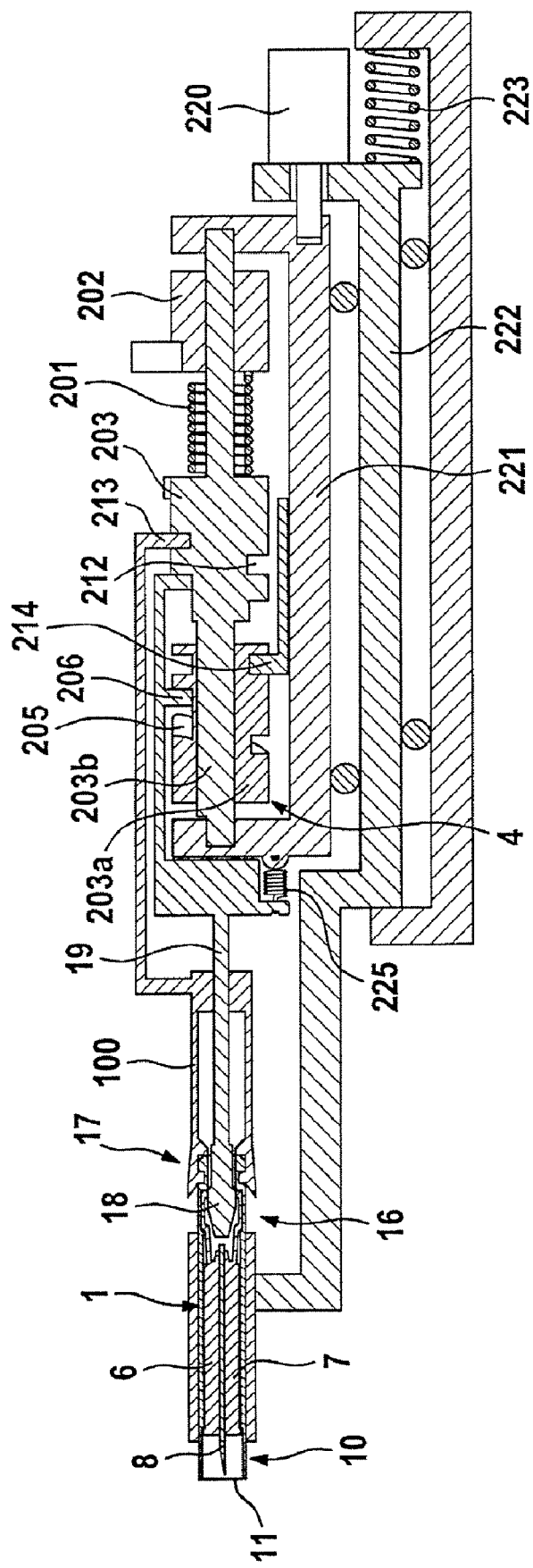
FIG. 23 is a longitudinal cross-sectional view of the puncturing system of FIG. 22.
Figure 24:
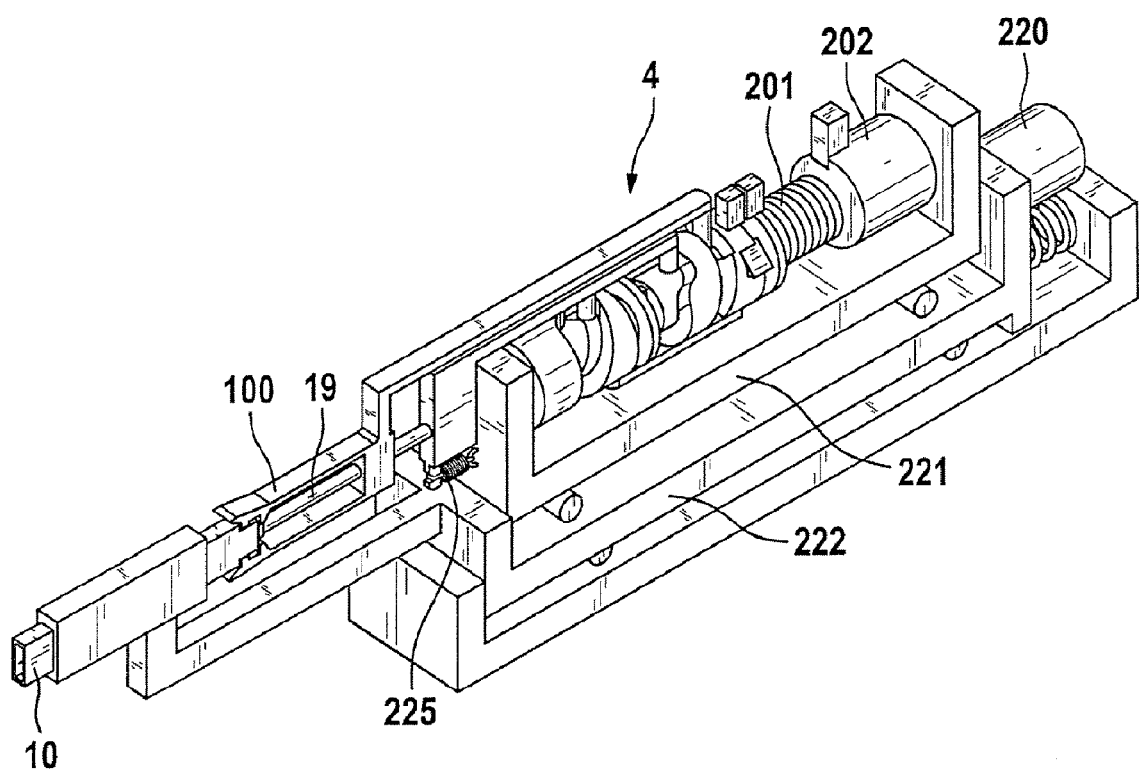
FIG. 24 is a perspective view of the puncturing system of FIG. 22.
Figure 27A:
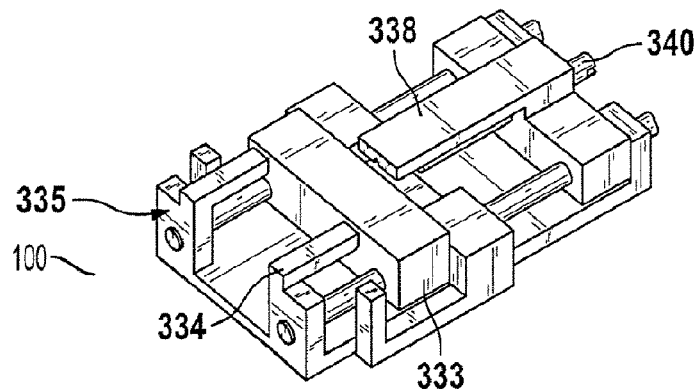
FIGS. 27 through 30 are perspective views (i.e., FIGS. 27A, 28A, 29A, and 30A) and partially cross-sectional side views (i.e., FIGS. 27B, 28B, 29B, and 30B) of another embodiment of a puncturing system illustrated in four operational positions.
Figure 27B:
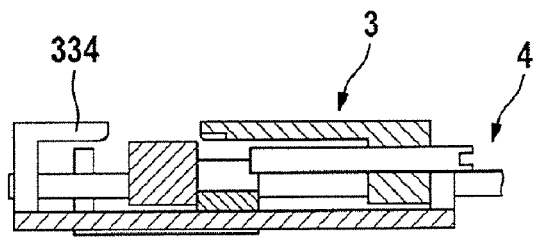

A further exemplary embodiment of a puncturing system, which has a puncturing profile with the special features described relative to FIG. 20, is shown in FIGS. 22-24. The puncturing unit 1 and the couplers 16 and 17 correspond to those of FIGS. 18 and 19. These elements and their function are therefore not described again. The puncturing drive 4 differs significantly from FIGS. 18 and 19. It is a rotor drive having stroke adaptation, as is explained in more detail hereinafter.

The puncturing drive 4 of the puncturing instrument 2 includes a drive spring 201, a cocking rotor 202 for cocking the drive spring, and a drive rotor 203 driven by the drive spring 201. The rotational movement of the drive rotor 203 is converted into the puncturing movement of the needle element 6 by means of a control unit in the form of a cam controller. A needle element control curve 205 is implemented as a groove in the drive rotor 203 and is traveled by a needle element control curve traveler 206 (in the form of a pin engaging in the control curve 205), which is connected to a connecting rod 19 and to which the needle element 6 is coupled.

The movement of the puncturing depth reference element 10 is also controlled by a cam controller comprising a reference control curve 212 and a reference control curve traveler 213. The reference control curve 212 is also implemented as a groove in the drive rotor 203. A control curve traveler 213, which is connected to the reference element holder 100, engages the control curve 212.

To set the puncturing depth, the distance of the two control curves 205 and 212 is adjustable by means of an adjustment device 214 in the form of an adjustable axial mount. The two control curves 205 and 212 are located on a first part 203a of the drive rotor 203 and on a second part 203b of the drive rotor 203, respectively. The distance between the first part 203a and the second part 203b of the drive rotor 203 can be varied by means of the adjustment device 214.

During usage, the puncturing instrument is pressed against the skin of the user by a housing skin contact area 33, which is schematically shown in FIG. 21 and encloses a housing opening 35. The distance between of the reference element 10 from the skin surface is subsequently determined for the purpose of (active) stroke adaptation. For this purpose, a first slide 221, displaceable in the piercing direction, is moved by an electric motor 220 toward the skin surface. The drive 4, including the needle element positioning part 16a formed by the connecting rod 19 and the reference element positioning part 17a formed by the reference element holder 100, is mounted on the first slide 221. The first slide 221 is moved forward until the reference element 10 contacts the skin. Contact may be detected electronically, for example, by an inductive or capacitive measurement. Thereafter, the first slide 221 is retracted again until there is a defined distance to the skin surface.

After a puncturing movement is triggered, the needle element positioning part 16a and the reference element positioning part 17a are moved forward by a rising flank of the corresponding control curves 205, 212 during the forward phase of the puncturing movement. While the needle 8 penetrates into the skin, the skin contact area 11 of the reference element 10 abuts against the skin so that a reference point for a precise piercing depth is defined.

To compensate for the Z variance, a stroke adaptor 38 is provided in this embodiment. In this particular embodiment, two stroke adaptor constructions are used in combination.

The first active stroke adaptation is implemented comprising detection of the position of the skin surface before a puncturing movement is triggered and subsequent adaptation of the puncturing movement to the previously detected position (thereby shifting the entire stroke path). This form of active stroke adaptation is advantageous not only in the embodiment shown, but also in other constructive implementations.

In addition, passive stroke adaptation is provided, which is implemented in this embodiment by mounting the first slide 221 such that it is displaceable in the longitudinal direction on a second slide 222, which may be shifted backwards against the force of a contact pressure control spring 223. Accordingly, a maximum contact pressure is defined, which may act on the skin via the reference element 10. This additional passive stroke adaptation is facultative.

After reaching the reversal point of the puncturing movement, the needle element positioning part 16a and the reference element positioning part 17a are retracted. The cam controller 205, 206 acting on the needle element positioning part has the special feature that the needle element control curve traveler 206 disengages during the retraction movement from its engagement in the corresponding control curve 205. This deviates from the usual design such that, the control curve traveler is not positively controlled along the entire control curve in such a manner that each position of the control curve traveler on the control curve corresponds to a defined longitudinal position of the rider and thus the element controlled thereby (needle element or reference element) in the piercing direction. Rather, the longitudinal position of the control curve traveler, and thus the controlled element, is at most delimited in one spatial direction (in the piercing direction or opposite to the piercing direction) when the control curve is disengaged, but is free at least in the opposite spatial direction. This is achieved in the embodiment shown by making the groove forming the control curve 205 wider so that the control curve traveler 206 is no longer guided there. During the retraction phase, the needle element positioning part 16a (and thus the needle element) is therefore not actively retracted by the needle element control curve traveler 206.

The retraction movement of the needle element positioning part 16a is instead caused by of a restoring spring 225. It couples the needle element positioning part 16a to the first slide 221 and thus also to the drive 4. During the retraction phase, the needle element positioning part 16a is therefore moved rearwardly by the restoring spring 225 relative to the drive until a second control curve traveler 226 connected thereto engages a second control curve 227, which is formed at the second part 203b of the drive rotor 203. The second control curve 227 thus forms a retraction limiter, by which the movement of the needle element 6 is stopped at the end of the first retraction section R1. This ensures a defined position of the needle element positioning part 16a in relation to the reference element positioning part 17a, in which the tip 13 of the needle 8 projects at a predefined residual puncturing depth from the skin contact area 11 of the puncturing depth reference element 10. After termination of the collection section S, the needle element 6 is pulled completely out of the skin by retracting the first slide 221 by an electric motor 220.

The embodiments shown in FIGS. 17-19 and 22-24 show that the puncturing depth reference element 10 does not have to be moved together with the needle element 6 during the entire forward phase (as in FIGS. 1 and 2, for example). Rather, it may be advantageous if the puncturing depth reference element 10 is only moved together (i.e., simultaneously, but not necessarily equally as fast) with the needle element 6 during at least part of the forward phase immediately preceding the reversal point. The length of the stroke (path segment in the piercing direction) by which the puncturing depth reference element 10 is moved together with the needle element 6 until reaching the reversal point is generally no more than 5 mm, and advantageously no more than between 2-3.5 mm. In the embodiment shown in FIGS. 17-19, this is achieved because the puncturing depth reference element 10 rests in a rest position on a reference element bearing 105 and is co-transported with the movement of the needle element 6 starting from this rest position, shortly before the needle element 6 reaches the reversal point. Other embodiments are possible, however, as shown in FIGS. 22-24.

Furthermore, it is advantageous if the time needed during the puncturing movement when the puncturing depth reference element 10 is moved together with the needle element during the forward phase (i.e., until reaching the reversal point) is short. This time is generally no more than 100 ms, but is more advantageous when between 10-50 ms.

It has been determined that the above-described measures, which may be used individually or in combination with one another, allow a precise control of the puncturing depth. In addition, with such a short pressure application onto the skin, the viscoelastic properties of the skin do not cause a substantial deterioration of the residual puncturing depth by a deformation of the skin. It is additionally advantageous if, in a puncturing profile similar to that shown in FIG. 20, the first retraction section R1, between reaching the reversal point (maximum puncturing depth) and beginning the collection section, lasts at most 2 seconds, and more advantageous if no more than between 0.5-1 second.

In the puncturing system shown in FIG. 25, the design of the puncturing unit and the couplers 16 and 17 are similar to these in FIGS. 18-19 and 22-24. These elements are again designated by the same reference numerals and are not described again.

Also related to the embodiment shown in FIGS. 18 and 19, the reference element positioning part 17a is formed by a reference element 100, which is movable in the longitudinal direction in the housing (not shown) and rests in the starting position of the puncturing movement shown on a reference element bearing 105. The reference element 100 and puncturing unit 1, connected thereto via the reference element coupler 17, are guided in the longitudinal direction in a housing part 301. The remaining housing is not shown. However, a housing skin contact area is also provided in this puncturing system, as is shown in FIGS. 2c and 22.

Another feature which is common to FIGS. 18 and 19 is that a ballistic puncturing drive 4 is used. However, in the embodiment shown in FIG. 25, it operates according to the "hammer-anvil principle", i.e., a component identified as a hammer 302 (only shown symbolically) is moved rapidly in the direction toward an anvil 303, which in turn is operationally linked via a coupling mechanism 3 to the puncturing unit 1.

In this embodiment, the reference element coupler 17 is again closed upon insertion of the puncturing unit 1. The reference element holder 100 forms a holder 27 for receiving a disposable puncturing unit 1. The needle element coupler 16 is closed only when the connecting rod 19 connected to the anvil 303 is moved forward. A co-transport device 103 is again provided here, which includes the two corresponding stops 101 and 125. The puncturing drive 4 is directly coupled only to the needle element 6 here, while the reference element 10 is coupled to the needle element 6 and thus indirectly to the puncturing drive 4 via the co-transport device 103 acting in the forward phase of the puncturing movement.

Deviating from the embodiments in FIGS. 18 and 19, the puncturing depth adjustment of FIG. 25 is implemented by a longitudinal displacement of a puncturing depth limit stop connected to the needle element 6 (not to the reference element 10). In the embodiment shown, a puncturing depth adjustment ring 305 is rotatable on a thread 306 of the connecting rod 19 and may thus be adjusted in its longitudinal position in relation to the needle element 6. The puncturing depth adjustment ring 305 is used for mounting a stop ring 307 elastically displaceable in the longitudinal direction on the connecting rod 19, the elasticity being provided by a metallic contact pressure spring 308.

When the anvil 303 is moved forward (to the left in FIG. 25) as a result of the impact of the hammer 302, the bidirectionally acting needle element coupler 16 closes. When the stop faces 101 and 125 are in contact, they form a unidirectionally acting coupler, which provides along with the elasticity caused by the spring 308, a connection between the connecting rod 19 (and thus the drive 4) and the reference element 10. The longitudinal dimensions of the components are adapted to one another such that in the subsequent movement phase up to the contact instant (incidence of the skin contact area of the puncturing depth reference element on the skin surface), the distance between the skin contact area 11 and the tip 13 of the needle element 6 is less than the desired (predefined) value of the puncturing depth. In this phase, the tip 13 of the needle element 6 is still located behind the skin contact area in the piercing direction and piercing into the skin occurs only after the contact instant.

Upon contacting the skin, the reference element 10 is stopped. The elasticity of the contact pressure spring 308 (i.e., the elasticity of the coupling between the puncturing depth reference element 10 and the puncturing drive 4) ensures that the skin contact area 11 is pressed against the skin at a pressure corresponding to the elasticity of the spring. This causes tensioning of the skin, while a further movement forward of the needle element is possible until the reversal point of the puncturing movement is reached.

In this embodiment, the required limiting movement of the needle element 6 is achieved such that the relative movement between the puncturing depth adjustment ring 306 and the stop ring 307 is stopped when stops 309 and 310 provided on these elements abut one another. The maximum movement path of the needle element 6 in relation to the reference element 10 is thus limited and the needle element 6 has at the reversal point a defined longitudinal position in the piercing direction in relation to the puncturing depth reference element 10. Accordingly, the stops 309 and 310 act as puncturing depth limiting stops. The stops 309 and 310, as well as the stops 101 and 125, form two unidirectionally acting couplers and abut against one another at the reversal point of the puncturing movement in such a manner that their relative distances define the puncturing depth.

The retraction phase of the puncturing movement is driven by a retraction spring 311, which rests on one side against a housing-fixed bearing part 312 and on the other side against the anvil 303. First the needle element 6 is drawn backwards so that the needle tip 13 is retracted behind the skin contact area 11 and the catch hook 25 again enters the catch profile 26, thereby fixing the longitudinal position of the needle element 6 in the puncturing depth reference element 10. The further rearward movement of the connecting rod 19 acts on the entire puncturing unit 1 until it is stopped by the contact of the reference element holder 100 with the reference element bearing 105.

In the final position, the puncturing depth reference element 10 is coupled to the puncturing drive 4 via a pair of corresponding stops 143, 144. In FIG. 25, the co-transport device 103 again acts bidirectionally, on one side by stops 101, 125 and 309, 310, and on the other side by stops 143 and 144. Deviating from FIGS. 18 and 19, however, this embodiment is not provided to achieve a defined residual puncturing depth, but rather to fix the reference element holder 100, and the reference element 10, in the position shown due to the operation of the stops 143, 144 in the retraction phase. The puncturing unit 1 may be pushed out and ejected from the holder 100 by an ejector (not shown here).

Actual testing of the embodiment of FIG. 25 has shown that a reproducible puncturing depth and an extremely low pain sensation are achieved therewith. According to the testing, this is to be attributed, inter alia, to the fact that the skin contact area of the puncturing depth reference element 10 exerts a pressure on the skin surface which is sufficient to tension the skin when the piercing occurs. Therefore, the puncturing drive 4 and the coupling mechanism 3 should be implemented in such a manner that, at the contact instant (i.e., instant contact between the skin contact area 11 and the skin surface), the tip 13 of the needle element 8 does not project at all, or projects only so slightly over the skin contact area such that the pressure of the skin contact area is already effective at the instant at which the needle tip 13 enters into the skin.

In this embodiment, it has been established that the longitudinal position of the needle element 8 and the skin contact area 11, as well as the pressure exerted by the skin contact area 11 (during at least part of the forward phase) on the skin surface, may be experimentally optimized in such a manner that the negative influence upon skin deformation caused by piercing the skin with the needle element 6 has on the reproducibility of the puncturing depth may be reduced. Experiments have shown that this is possible such that skin deformation no longer has an influence on the puncturing depth. This is supported by the fact that the actual depth of the puncture into the skin corresponds with the set puncturing depth of the device (distance between the tip 13 and the skin contact area 11). It has been established that without the measures described herein, the actual puncturing depth into the skin was more than 0.3 mm smaller than the puncturing depth set on the device.

In this context, the size of the skin contact area also plays a role. Its diameter should be at least 1.5 mm, but not more than 6 mm. The skin contact area 11 must be designed with a soft edge. In particular, it would be disadvantageous if a sharp edge was present in the region of the skin contact area 11 after removal of the insertion aid 30, as is unavoidable when using the breakline design common in this context (having a weak line made of thin plastic). In one embodiment shown, the connection between the insertion aid 30 and the puncturing depth reference element 10 is therefore provided by a connection profile 30a made of soft, highly-elastic plastic. However, other embodiments are also possible if it is ensured that the skin contact area is free of broken edges after removal of the insertion aid 30. Advantageously, the skin contact area is convexly curved in the vicinity of the needle element exit opening.

The effect of skin tensioning and the reproducibility of the puncturing depth is a function of a plurality of factors. In general, the pressure by which the skin contact area 11 of the puncturing depth reference element 10 is pressed against the skin surface near the end of the forward phase should be high enough that the skin deformation caused by piercing the needle element into the skin ("denting") has no interfering effect on the reproducibility of the puncturing depth. This pressure should be at least 1 $N/cm^2$, but advantageously between 3-5 $N/cm^2$, and especially preferably at least 5 $N/cm^2$. It has been established that the internal pressure in the tissue resulting from this contact pressure minimizes negative influences which denting of the skin, upon piercing of the needle into the skin surface, normally produces. Therefore, good reproducibility of the puncturing depth is achieved and low pain sensation results.

It is to be assumed that the indirect coupling of the puncturing depth reference element 10 to the drive 4 via the co-transport device 103 and/or the elastic coupling and pressure control caused by the metal contact pressure spring 308 also provides a significant contribution to the function of the described puncturing system. The spring is installed pretensioned in such a manner that it acts, already in its maximum expanded state, with the desired minimum force. The force variation per unit of length (spring constant) is at most 0.1 N/mm.

The co-transport device (in particular, an elastic co-transport device) can also be implemented inside the puncturing unit itself. In this case, corresponding stops can be provided on the elements movable in relation to one another (needle element and puncturing depth reference element). In the case of an elastic co-transport device, a spring may be provided which is supported on one side of the needle element and on the other side of the puncturing depth reference element.

The puncturing system shown in FIGS. 26 to 30 is distinguishable from the above-described embodiments because the needle elements 6, which are implemented here as simple metallic, needle-shaped lancets 330, are combined to form a needle element strip 331 (FIG. 26). The needle element strip 331 has a carrier film 328, which the rear end (facing away from the tip 13) of each of the lancets 330 is fixed by adhesive. A cover film 329 covers the lancets and thus seals them hygienically. The assembly (connecting) of lancets in the form of strips is generally known, for example, from German Patent No. 28 03 345 and document EP 1 360 935.

It is important that the carrier film 328 and the cover film 329 of the needle element strip 331 are very thin. The thickness of the carrier film 328 is no more than 100 µm, and advantageously between 30-50 µm. The thickness of the cover film 329 should be no more than 50 µm, and advantageously between 15-25 µm.

The needle element strip 331 is used not only to provide sterile packaging of a plurality of needle elements and for supplying them for use in a cost-effective manner. Rather, the carrier film 328 also forms a hygienic layer for the skin contact area during the piercing. Thus, it is a component of the puncturing depth reference element. A suitable embodiment of the puncturing system is shown in four operational positions in FIGS. 27 to 30.

Figure 28A:
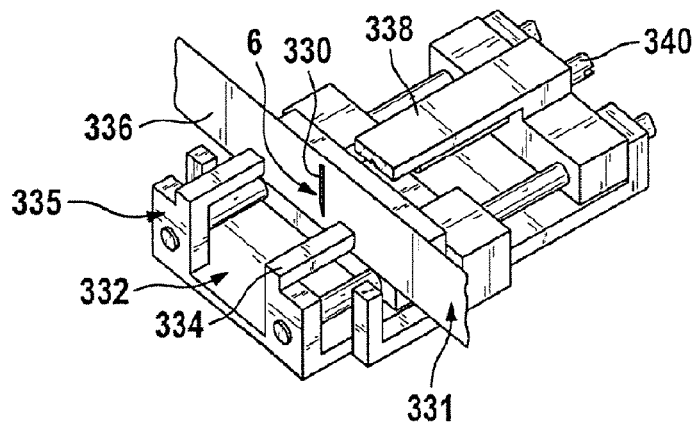
Figure 28B:
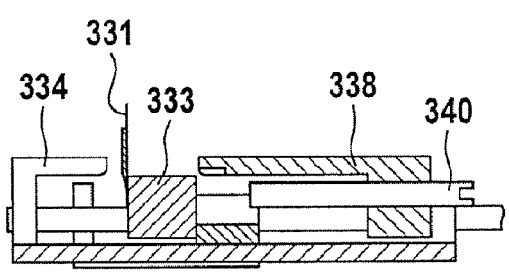
Figure 29A:
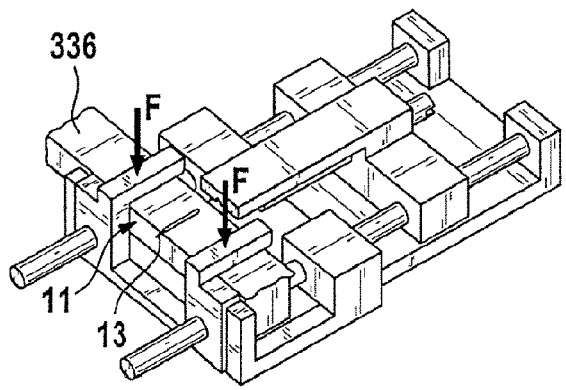
Figure 29B:
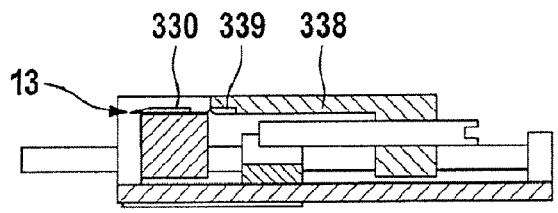

The needle element strip 331 is transported by a transport device (not shown) in a step-by-step manner in which one lancet 330 at a time is located at a puncture station 332 in front of a reference element base part 333 (FIG. 28). A strip retainer 334 is a component of a puncture preparation device identified as 335, in which a needle element 6 located at the puncture station 332 is brought into a puncture position in which its tip 13 is exposed and oriented in the piercing direction, while the carrier film 328 covers the reference element base part 333 in the area surrounding the needle tip 13 (FIG. 29). In this embodiment, the strip retainer 334 is L-shaped in a plane parallel to the piercing direction and it is shifted over the needle element strip 331 in such a manner that the strip is bent at a right angle. Thereafter, a part of the strip covers the front edge of the reference element base part 333 (to the left in FIG. 29A) and forms the skin contact area 11 there. This exemplary embodiment provides that not the entire piercing depth reference element 10 is a single-use (disposable) item, but rather only the element which has the skin contact area.

Figure 30A:
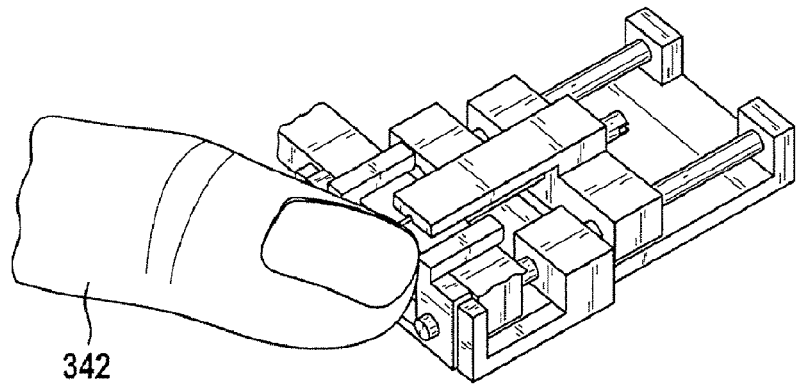
Figure 30B:
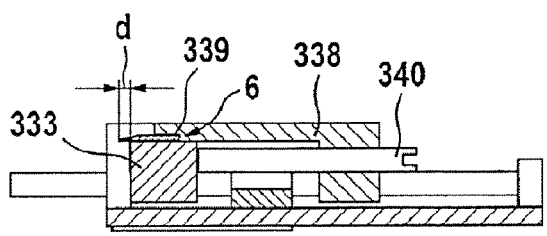

A lancet gripper 338 is moved against the lancet from the rear (from right to left) and is used to move one lancet at a time. A recess 339 of the lancet gripper 338 encloses the rear end of the lancet 330 (FIG. 30). The movement path of the lancet gripper 338 in relation to the reference element base part 333 is limited by a puncturing depth adjusting screw 340. When the front end of the puncturing depth adjusting screw 340 abuts against the reference element base part 333, further movement of the lancet gripper 338 forward (to the left in the figures) causes a corresponding forward movement of the reference element base part 333 and the carrier film 328, with the skin contact area (i.e., the reference element formed as a whole by the carrier film 328 and the base part), together with the lancet 330. The forward movement is also the same as the puncturing movement direction. The needle protruding distance d shown in FIG. 30B defines the puncturing depth. The piercing into a finger 342 shown in FIG. 30A is performed during the forward movement.

During actual testing of this embodiment, it has been established that, surprisingly, a reproducible puncturing depth may result if thin films are used (having the preferred thicknesses specified above). This is the case even if the carrier film 328 or residues of the cover film 329 do not form a smooth layer in the region of the skin contact area 11, but rather wrinkle, for example. Therefore, the advantages in this embodiment may ideally be combined with the advantages of a needle element strip. This is particularly true if the strip not only carries needle elements (lancets), but also alternating test elements, and the system is implemented as an integrated system which not only performs blood withdrawal, but rather also provides analysis. A combined analysis element strip allows the simple implementation of transport functions necessary in such integrated systems, while simultaneously avoiding hygienic problems by using the carrier strip as a component of the reference element in the region of the skin contact area. The test elements are favorably produced separately because of the sensitivity of the reagents contained therein and are attached to the carrier film 328 by adhesive.

Figure 31:
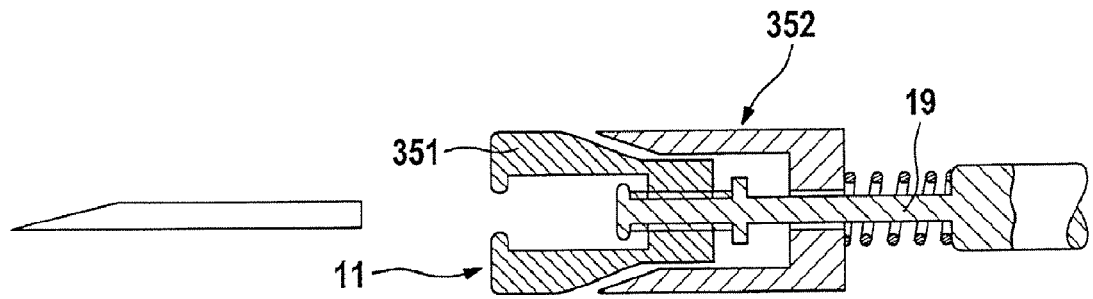
FIGS. 31 through 33 are partial cross-sectional views of a further embodiment of a puncturing system in three operational positions.
Figure 32:
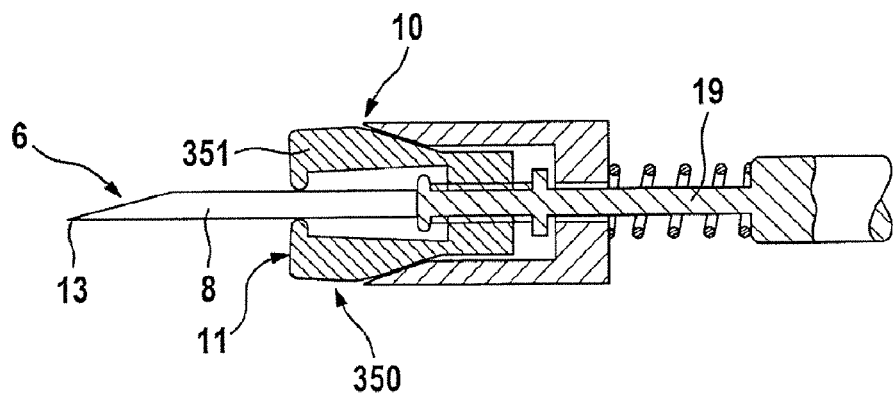
Figure 33:
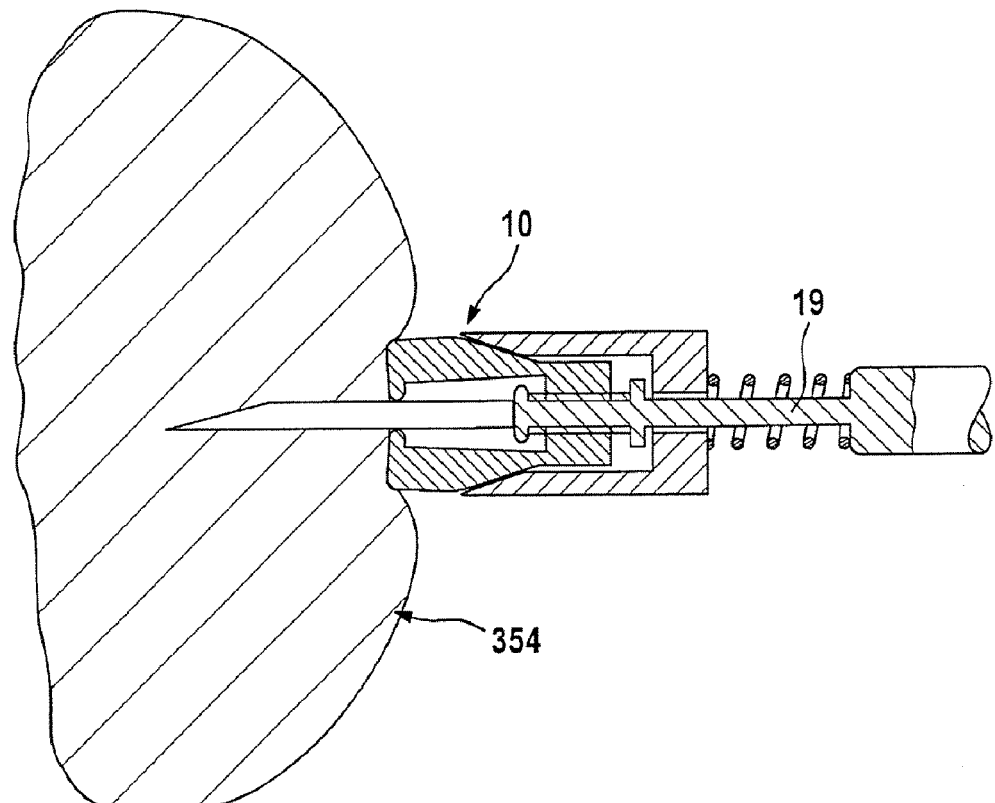

FIGS. 31-33 show those parts of another embodiment of a puncturing system which are important for its function. In this embodiment the coupling mechanism 3, by which a needle element 6 and a reference element 10 are connected via a connecting rod 19 to a drive (not shown), is implemented in an especially simple and space-saving way. The needle element 6 only comprises a metal needle 8. For the coupling mechanism shown, it is characteristic that the puncturing depth reference element 10 simultaneously forms a gripper 350 which encloses the needle element 6 like pincers and thus fixes it. In the embodiment shown, gripper arms 351 of the gripper 350 are actuated by a closing mechanism 352, which does not have to be explained in more detail, because suitable mechanical principles are known (for example, for holding leads in a mechanical pencil). The gripper element is implemented in such a manner that it may be pushed over the needle element 6 in the open state (FIG. 31) and the gripper arms 351 may subsequently be closed, to hold the needle element 8 by lateral pressure in the direction toward its center (FIG. 32). In the simplest case, the skin contact area 11 of the puncturing depth reference element 10 which presses against the skin surface 354 during piercing (FIG. 33), is formed by an appropriately shaped front face of the gripper 350.

In the embodiment shown in FIGS. 31 through 33, the puncturing depth reference element 10 is simultaneously used as a holder for the needle element. The gripper 350 forms a fixing means, by which the needle element 6 may be fixed in different longitudinal positions in relation to the puncturing depth reference element 10 for adjusting the puncturing depth. In the embodiment shown, the puncturing depth is adjusted by rotating the connecting rod 19 in relation to the gripper arms 351. However, other implementations of the described design principle are possible in regard to the fixing means.

In this case, the skin contact area 11 is provided at one of the reusable parts of the puncturing instrument. To avoid contamination and improve the hygienic conditions, it may be advantageous to provide a disposable protective layer on the forward end of the gripper, for example, in the form of a film or in the form of replaceable caps made of plastic. In this case, the gripper 350 does not directly form the skin contact area, but rather functions as a reference element base part whose surface (similarly as in FIGS. 26 through 30) is covered by the layer and has the actual skin contact area.

The illustrated embodiments show that numerous aspects are possible. This relates, for example, to the couplers, which provide separate connections of the needle element and the puncturing depth reference element to the corresponding positioning parts of the coupling mechanism. However, all embodiments share the feature that at least the needle element, but also the reference element, has a coupler structure which cooperates with a corresponding coupler profile of the positioning part. The terms "coupler structure" and "coupler profile" generally identify any design of the cited elements by which an at least unidirectional, but also bidirectional coupling, is produced in the meaning explained.

Numerous embodiments are also possible in regard to the point in time at which the coupling occurs. In particular, implementations may be advantageous for many intended uses in which the coupling by the needle element coupler and/or the reference element coupler occurs only during the forward phase of the puncturing movement. Embodiments in which these couplers open during the retraction phase of the puncturing movement before reaching the starting position of the puncturing drive are also advantageous for many intended uses.

Of course, instead of the coiled springs shown in the figures, other spring devices may also be used, such as leaf springs, disk springs, or mutually repelling magnets. The drive during the retraction phase is provided by separate spring elements belonging to the same or different type of spring.

As explained at the beginning, the present invention is particularly suitable for integrated systems in which the functions of obtaining blood and of analysis are unified in one device. In the case of a microsampler, this integration is made possible by providing the reagents and other components required for the analysis in its sample receiving area. In this regard, microsamplers suitable for the present invention do not differ from known systems. Puncturing units without capillary channels may also be used advantageously in integrated systems. In this case, the puncturing unit is retracted rapidly after the puncturing step so that the sample liquid exiting from the skin may flow into a capillary channel of an analysis element, and once inside the puncturing instrument, is brought into contact with the sample liquid exiting from the skin.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A lancing system, comprising:
   a housing having a drive unit;
   a puncturing unit removably receivable in the housing and operable by the drive unit, the puncturing unit comprising a needle and a depth reference element that includes a skin contact area configured to contact the skin being punctured;
   a coupling mechanism for connecting the puncturing unit to the drive unit, the coupling mechanism comprising a needle coupler having a needle stop that cooperates with a corresponding stop of the needle and a reference element coupler having a reference element stop that cooperates with a corresponding stop of the depth reference element;
   wherein, during use of the lancing system, the drive unit drives the needle in a puncturing movement having a forward phase during which the needle is moved in a puncturing direction until its tip penetrates the skin, a retraction phase during which the needle is retracted from the skin, and a reversal point between the forward and retraction phases, the puncturing depth of the needle corresponding to the distance between the contact area and the tip of the needle at the reversal point;
   wherein, the drive unit drives the depth reference element with the needle during at least part of the puncturing movement; and
   further wherein, the puncturing depth is adjustable by changing a distance (d) existing at the reversal point between the skin contact area and the tip of the needle.

2. The lancing system of claim 1, wherein the housing includes a stroke adaptor for adapting the puncturing movement to the contour of a body part.

3. The lancing system of claim 2, wherein the stroke adapter comprises an elastic element.

4. The lancing system of claim 2, wherein the stroke adapter comprises a detector configured for detecting the position of the body part during the puncturing movement and a control unit configured for controlling the puncturing movement based on the detected position.

5. The lancing system of claim 1, wherein the position of the needle is fixed relative to the depth reference element during the puncturing movement.

6. The lancing system of claim 1, wherein the needle moves relative to the depth reference element during the puncturing movement.

7. The lancing system of claim 1, wherein, before the contact area contacts a body part, the contact area is positioned ahead of the tip in the piercing direction.

8. The lancing system of claim 1, wherein the housing comprises an opening surrounded by a housing contact surface that abuts against a body part during the puncturing movement.

9. The lancing system of claim 1, wherein the contact area is configured to apply pressure against a body part.

10. The lancing system of claim 1, wherein the position of the needle at the reversal point is determined by contact between the needle stop of the needle coupler and the corresponding stop of the needle.

11. The lancing system of claim 1, wherein the position of the depth reference element at the reversal point is determined by contact between the reference element stop of the reference element coupler and the corresponding stop of the depth reference element.

12. The lancing system of claim 1, further comprising a co-transport device, the co-transport device connecting the depth reference element to the needle during at least part of the forward phase.

13. The lancing system of claim 12, wherein the co-transport device comprises a first limit stop and a second limit stop, the first limit stop being coupled to the needle and the second limit stop being connected to the depth reference element.

14. The lancing system of claim 13, wherein, during the puncturing movement, the reversal point is reached when the first limit stop contacts the second limit stop.

15. The lancing system of claim 12, wherein the co-transport device comprises a needle retraction stop and a depth reference retraction stop, the needle retraction stop being coupled to the needle and the depth reference retraction stop being coupled to the depth reference element.

16. The lancing system of claim 15, wherein, during the retraction phase, the needle retraction stop contacts the depth reference retraction stop and the corresponding distance between the tip and the depth reference element at the time of contact defines a residual puncturing depth.

17. The lancing system of claim 16, wherein the tip retracts from the reversal point to the residual puncturing depth in 0.5 seconds to 2 seconds.

18. The lancing system of claim 1, wherein the depth reference element is elastically connected to the needle during at least part of the forward phase.

19. The lancing system of claim 1, wherein the contact area has a diameter between 1.5 mm and 6 mm.

20. The lancing system of claim 1, wherein the depth reference element moves during at least part of the forward phase with the needle for between 10 ms and 100 ms.

21. The lancing system of claim 1, wherein the needle comprises a capillary channel configured to transport body fluid from a body part into a sample receiving area of the needle.

22. The lancing system of claim 21, wherein the needle comprises a window configured to optically measure the body fluid in a sample receiving area.

23. The lancing system of claim 21, wherein the needle comprises electrical contacts configured to perform electrical measurements on the body fluid in a sample receiving area.

24. The lancing system of claim 1, wherein the housing comprises a holder, the holder interchangeably connecting the puncturing unit to the drive unit.

25. The lancing system of claim 1, wherein the depth reference element comprises a body having an end portion that defines the contact area, the body at least partially enclosing the needle.

26. The lancing system of claim 1, wherein the needle is disposed in a magazine.

27. The lancing system of claim 26, wherein the needle is moveable to an operating position in which the needle is moveable with the depth reference element during at least part of the puncturing movement.

28. The lancing system of claim 1, wherein the needle comprises a plurality of needles, the lancing system further comprising a strip that holds the plurality of needles.

29. The lancing system of claim 28, further comprising a transport device for moving one of the plurality of needles to a puncture station.

30. Lancing system of claim 29, wherein the depth reference element holds the needle positioned at the puncture station, the position of the needle positioned at the puncture station being adjustable relative to the depth reference element to adjust the puncturing depth.

31. The lancing system of claim 28, further comprising a carrier film that protects the tips of the plurality of needles.

32. The lancing system of claim 31, wherein the plurality of needles are sealed by a cover film.

33. The lancing system of claim 1, wherein the needle and the depth reference element are movable relative to one another in the piercing direction to adjust the puncturing depth.

34. A method of withdrawing body fluid from a body part with a puncturing unit having a needle and a depth reference element with a contact surface, the method comprising:
  connecting the puncturing unit to a lancing device having a drive unit, the connection comprising a coupling mechanism comprising a needle coupler having a needle stop that cooperates with a corresponding stop of the needle and a reference element coupler having a reference element stop that cooperates with a corresponding stop of the depth reference element;
  adjusting the distance between the contact surface and the tip of the needle;
  using the drive unit to move the needle in a puncturing movement to puncture the body part, the puncturing movement having a forward phase, a retraction phase, and a reversal point therebetween;
  contacting the body part with the contact surface during the puncturing movement; and
  moving the depth reference element together with the needle element during at least part of the puncturing movement;
  wherein the puncturing depth of the needle corresponds to the distance between the contact surface and the tip of the needle at the reversal point.

35. The method of claim 34, wherein the contacting step further comprises contacting the body part with the contact surface before the needle reaches the reversal point and then moving the tip in the piercing direction past the contact surface and into the body part until the reversal point is reached.

36. The method of claim 34, further comprising moving the needle relative to the depth reference element during at least part of the puncturing movement.

37. The method of claim 34, further comprising detecting the position of the body part before triggering the puncturing movement.

38. The method of claim 34, further comprising adjusting the position of the reversal point with a stroke adapter of the lancing device to compensate for the contour of the body part.

39. The method of claim 34, wherein after the reversal point is reached, the tip is retracted and the distance between the contact area and the tip is reduced to and maintained at a residual puncturing depth.

40. A lancing system for withdrawing a body fluid from the skin of a human or animal, comprising:
  a housing having a puncturing drive;
  a puncturing unit comprising a needle for piercing into the skin in a piercing direction and a puncturing depth reference element having a skin contact area that contacts the skin; and
  a coupling mechanism for connecting the puncturing unit to the puncturing drive, the coupling mechanism comprising a needle coupler having a needle stop that cooperates with a corresponding stop of the needle and a reference element coupler having a reference element stop that cooperates with a corresponding stop of the puncturing depth reference element;
  wherein:
  (a) during use of the lancing system, the puncturing drive drives the needle in a puncturing movement having a forward phase during which the needle is moved in a puncturing direction until its tip penetrates the skin, a retraction phase during which the needle is retracted from the skin, and a reversal point between the forward and retraction phases; and
  (b) the distance between the skin contact area and the tip of the needle is adjustable to establish a predefined puncturing depth corresponding to the distance between the skin contact area and the needle tip at the reversal point, whereby the predefined puncturing depth is ensured and the maximum puncturing depth of the needle in the skin is limited.

41. Lancing system according to claim 40, wherein the needle element has a capillary channel through which body fluid may flow from the skin into a sample receiving area of the needle element.

42. Lancing system according to claim 41, further comprising a window for allowing an optical measurement on a fluid in the sample receiving area.

43. Lancing system according to claim 41, further comprising electrical contacts for performing an electrical measurement on a fluid in the sample receiving area.

44. Lancing system according to claim 40, wherein the coupling mechanism removably and interchangeably connects the puncturing unit to the puncturing drive.

* * * * *